United States Patent
Kim et al.

(10) Patent No.: US 11,561,222 B2
(45) Date of Patent: Jan. 24, 2023

(54) METHOD FOR DIAGNOSIS OF BILE DUCT CANCER USING METHIONYL-TRNA SYNTHETASE IN BILE DUCT CELL

(71) Applicant: ONCOTAG DIAGNOSTICS CO., LTD., Suwon (KR)

(72) Inventors: Sunghoon Kim, Seoul (KR); Nam Hoon Kwon, Gyeonggi-do (KR); Dong Ki Lee, Gyeonggi-do (KR); Beom Jin Lim, Seoul (KR); Sung Ill Jang, Seoul (KR)

(73) Assignee: ONCOTAG DIAGNOSTICS CO., LTD., Suwon (KR)

( * ) Notice: Subject to any disclaimer, the term of this patent is extended or adjusted under 35 U.S.C. 154(b) by 465 days.

(21) Appl. No.: 16/679,652

(22) Filed: Nov. 11, 2019

(65) Prior Publication Data

US 2020/0225234 A1 Jul. 16, 2020

Related U.S. Application Data

(63) Continuation-in-part of application No. PCT/KR2018/005443, filed on May 11, 2018.

(51) Int. Cl.
| | |
|---|---|
| *G01N 33/574* | (2006.01) |
| *C07K 16/40* | (2006.01) |
| *C12N 9/00* | (2006.01) |
| *G01N 1/30* | (2006.01) |
| *G01N 33/50* | (2006.01) |
| *G01N 33/573* | (2006.01) |

(52) U.S. Cl.
CPC ....... *G01N 33/57407* (2013.01); *C07K 16/40* (2013.01); *C12N 9/93* (2013.01); *C12Y 601/0101* (2013.01); *G01N 1/30* (2013.01); *G01N 33/5091* (2013.01); *G01N 33/573* (2013.01); *C07K 2317/56* (2013.01)

(58) Field of Classification Search
CPC .................. G01N 33/57407; G01N 33/5091
See application file for complete search history.

(56) References Cited

U.S. PATENT DOCUMENTS

| 8,563,235 B2 | 10/2013 | Kikkawa et al. |
|---|---|---|
| 2011/0108722 A1 | 5/2011 | Kikkawa et al. |
| 2012/0065089 A1 | 3/2012 | Kuno et al. |
| 2014/0031257 A1* | 1/2014 | Lothe .................. C12Q 1/6886 506/9 |
| 2014/0235494 A1 | 8/2014 | Schmidt et al. |

FOREIGN PATENT DOCUMENTS

| JP | 2009528835 A | 8/2009 |
|---|---|---|
| JP | 2011-099858 A | 5/2011 |
| JP | 2012-237685 A | 12/2012 |
| KR | 10-2005-0099581 A | 10/2005 |
| WO | 2007102146 A2 | 9/2007 |
| WO | 2008007818 A1 | 1/2008 |
| WO | 2011072265 A1 | 6/2011 |
| WO | 2011140135 A2 | 11/2011 |
| WO | 2013043012 A2 | 3/2013 |
| WO | 2013190081 A1 | 12/2013 |

OTHER PUBLICATIONS

Park et al, J Korean Sci, 26:1023-1030, 2011.*
English Abstract of JP 2012-237685.
English Abstract of KR 10-2005-0099581.
Seo et al. "Genomic medicine: bringing biomarkers to clinical medicine" Current Opinion in Chemical Biology 2005, 9:381-386.
Dec. 22, 2020 (EP) European Search Report Application No. 18799158.3.
Aug. 28, 2018 (WO)—International Search Report Application No. PCT/KR2018/005443.
Murakami et al. "Comprehensive analysis of transcriptome and metabolome analysis in Intrahepatic Cholangiocarcinoma and Hepatocellular Carcinoma" Scientific Reports, 5:16294. DOI: 10.1038/srep16294.

* cited by examiner

*Primary Examiner* — Mark Halvorson
(74) *Attorney, Agent, or Firm* — Banner & Witcoff, Ltd.

(57) ABSTRACT

The present invention relates to a method for diagnosis of bile duct cancer, using methionyl-tRNA synthetase (MRS) in bile duct cells of a latent patient.

11 Claims, 8 Drawing Sheets
(4 of 8 Drawing Sheet(s) Filed in Color)

Specification includes a Sequence Listing.

METHOD FOR DIAGNOSIS OF BILE DUCT CANCER USING METHIONYL-TRNA SYNTHETASE IN BILE DUCT CELL

CROSS-REFERENCE TO RELATED APPLICATIONS

This application is a continuation-in-part of PCT patent application Ser. No. PCT/KR2018/005443, filed on May 11, 2018, which claims a priority from Korean Patent Application No. 10-2017-0059318, filed on May 12, 2017 filed with the Korean Intellectual Property Office. The disclosures of the priority application are herein incorporated by reference in its entirety.

SEQUENCE LISTING

The instant application contains a Sequence Listing which has been filed electronically in ASCII format and is hereby incorporated by reference in its entirety. Said ASCII copy, created on Feb. 27, 2020, is named 009041_00004_US_SL.txt and is 22,966 bytes in size.

BACKGROUND

Field

The present invention relates to a method for diagnosing bile duct cancer by using methionyl-tRNA synthetase (MRS). More specifically, the present invention relates to a composition for diagnosing bile duct cancer, the composition comprising an agent for measuring the expression level of a methionyl-tRNA synthetase protein, a diagnostic kit, and a method for qualitatively or quantitatively analyzing MRS to provide information necessary for the diagnosis of a bile duct cancer.

Discussion of the Background

This application claims priority from and the benefit of Korean Patent Application No. 10-2017-0059318 filed on 12 May 2017, which is hereby incorporated by reference herein in its entirety.

Bile duct cancer, with an incidence rate of 6.3 cases in a population of 100,000, ranks the 9th among all cancers, but has a poor prognosis, ranking as the sixth-leading cause of cancer death in Korea. The usual course of care before definite diagnosis of bile duct cancer is as follows. When a patient generally comes to the hospital with symptoms, such as jaundice, abdominal discomfort, and weight loss, the patient is primarily suspected of having bile duct cancer through imaging examinations, such as abdominal ultrasound (US), endoscopic ultrasound (EUS), abdominal computed tomography (CT), or abdominal magnetic resonance imaging (MRI). In fact, the imaging examinations are effective only in the diagnosis of mass-forming bile duct cancer, but the diagnosis of non-mass-forming bile duct cancer through imaging examinations alone is difficult. Ultimately, pathological examinations are required for definite diagnosis of bile duct cancer. In other words, the types of bile duct cancer that may occur are divided into a mass-forming type and a non-mass-forming type (a periductal-infiltrating type and an intraductal-growing type). In the presence of a mass accessible by abdominal ultrasound or abdominal computed tomography, the mass can be subjected to a biopsy using such imaging examinations. However, if such a mass visible through imaging is absent or the mass is difficult to access, that is, in cases of the periductal-infiltrating type and intraductal-growing type, a biopsy or cytodiagnosis is performed through access to bile ducts using endoscopic retrograde cholangiogram or percutaneous transhepatic biliary drainage.

The term "pathological examination" refers to an examination that attempts to elucidate the origin of a disease mainly from a morphological point of view by using harvested cells, tissues, or organs. Pathological examination is an important type of examination applied to the diagnosis of a disease by grasping macroscopic findings, optical or electronic retrieval, or the like. Such pathological examination includes histopathological examination and cytopathological examination. Biopsy methods for bile duct cancer includes abdominal ultrasound-guided biopsy, abdominal computed tomography-guided biopsy, or biopsy through endoscopic retrograde cholangiogram (ERCP) or percutaneous transhepatic biliary drainage, and cytology methods include brush cytology through endoscopic retrograde cholangiogram or percutaneous transhepatic biliary drainage, and cytodiagnosis in bile.

Meanwhile, biopsy and cytodiagnosis have many differences therebetween, and it is known that biopsy and cytodiagnosis show many differences in diagnostic sensitivity and specificity in assays using well-known cancer markers. Therefore, with respect to conventionally known bile duct cancer markers, there is an additional issue of whether the markers can substantially attain effective diagnosis for specific specimens (tissues or cells).

In biopsy, a target site is endoscopically observed, or a predetermined cell tissue of about $1-10^9$ cells is harvested from the tissue suspected of being transformed into cancer and then cancer diagnosis is performed through a biochemical manner, such as staining. Such a biopsy is known to make it comparatively easy to make a definite diagnosis of cancer present in a particular region through comparison with surrounding structures or cells. Some researchers have reported study results on the number of samples that should be taken for tissue biopsy in order to increase the diagnostic sensitivity for bile duct cancer (Kawashima H, Itoh A, Ohno E, Goto H, Hirooka Y. Transpapillary biliary forceps biopsy to distinguish benign biliary stricture from malignancy: how many tissue samples should be obtained?, Dig. Endosc. 2012; 24 Suppl 1:22-27). It has been reported that when three or more specimens are harvested, the probability of a false positive is decreased to 0%, and if four or more harvested biopsy specimens are positive, a definite diagnosis of 100% positive can be made. Therefore, at least three tissue specimens need to be obtained for diagnosis of a malignant bile duct disease. However, increasing the number of biopsy specimens increases the physical burden on patients.

The distinction between cells or tissues of other benign bile duct diseases and cells or tissues of bile duct cancer is dependent on hematoxylin and eosin staining (HE stain), Papanicolaou staining (Pap stain), or the like, and these methods are reported to have a low diagnostic sensitivity of 40-60%. Moreover, there is a big problem in that pathological examinations, in which a definitive diagnosis of bile duct cancer is made through staining or the like after in-vitro extraction of cells or tissues, have lower sensitivity than non-invasive magnetic resonance imaging. Xu et al. reported sensitivity and specificity of respective diagnostic methods in patients suspected of malignant bile duct strictures (Xu M M, Sethi A. Diagnosing Biliary Malignancy. Gastrointest. Endosc. Clin. N. Am. 2015; 25:677-90). According to the above literature, non-invasive magnetic resonance cholangiopancreatography (MRCP) shows a sensitivity of 80%, but a low specificity of 70-85%, and therefore, both biopsy and cytodiagnosis are necessary for definite diagnosis. Various ranges of sensitivity for cholangiocarcinoma (CCA) have been reported, for example, the sole implementation of brush cytology using endoscopic retrograde cholangiogram (ERCP) results in a low sensitivity of 23-56%, and the sole implementation of biliary biopsy using ERCP results in a sensitivity of 44-89%. The co-implementation of brush cytology and biliary biopsy shows an increased sensitivity of up to 70%, which is still lower than the sensitivity of non-invasive MRCP.

Several diseases occurring in bile ducts, including bile duct cancer, are often accompanied by bile duct strictures, and it is difficult to make a differential diagnosis as to whether a corresponding area is malignancy (bile duct cancer) or other benign bile duct disease in a patient with bile duct strictures. Accurate diagnosis of bile duct strictures is most important in determining the direction of treatment, and makes it possible to avoid unnecessary surgery or treatment and suggest the most appropriate therapy for the patient. The narrow bile duct lumen and fibrosis are main factors that make it difficult to diagnose bile duct diseases. In the past, cytology was mainly conducted by suction of bile during endoscopic retrograde cholangiogram, percutaneous transhepatic biliary drainage, or the like. The cell specimens obtained through such a method had low cellularity and most underwent denaturation or autolysis, and thus cells usable for diagnosis have been difficult to obtain (Soyoung Jin et al., Availability of Biliary Brushing Cytology in pancreaticobiliary diseases, The Korean Journal of Cytopathology 17 (1): 38-45 2006). Therefore, biliary brush cytology, wherein a stricture is identified during endoscopic retrograde cholangiogram and a cell specimen is directly obtained using a brush from a site suspected of a lesion, has become common. The term "cytodiagnosis" refers to a diagnosis of a disease by the examination of cells mainly using an optical or phase microscope. Cytodiagnosis has limitations in making a definite diagnosis since comparison with surrounding structures or cells is difficult. Moreover, such an examination at the cellular level does not increase the diagnostic efficiency simply by increasing the number of cells. Specifically, Jo Y G, et al. compared examination results between cell-block techniques and general brush cytology. Specifically, the diagnostic efficiency was compared between a sample prepared by directly smearing general cells obtained from brush cytology (direct smear) and a sample prepared by collecting brush cytology into cell blocks, and as a result, the two methods showed no difference in sensitivity or specificity (Jo Y G, et al. Diagnostic accuracy of brush cytology with direct smear and cell-block techniques according to preparation order and tumor characteristics in biliary strictures. Korean J. Gastroenterol 2014; 63:223-30). In addition, Bang K B et al. reported that there was no difference in sensitivity or specificity in a study comparing cytodiagnosis using a brush and cytodiagnosis using a basket (Bang K B, Kim H J, Park J H, et al. Comparison of brush and basket cytology in differential diagnosis of bile duct stricture at endoscopic retrograde cholangiopancreatography. Hepatobiliary Pancreat. Dis. Int. 2014; 13:622-7.)

Difficulty in identifying atypical cells is also one of the obstacles in pathological examination of in-vivo isolated cells. Since Melamed et al., announced, as squamous cell atypia, a cell change which is not an inflammatory change but is insufficient to diagnose dysplasia, in 1976, there has been much controversy over the diagnosis, interpretation, and treatment strategy of atypical cells. For the resolution of controversy, the Bethesda System (TBS) was established. TBS extremely restricts the use of the term "atypical cells" so that the term can be used only in cases where the cell change cannot be diagnosed to be inflammatory, premalignant, or tumorigenic, and is of undetermined significance. The therapeutic strategy for atypical cells is difficult because there may be different views therefor. Actually, there is a problem in that in most cases, there are examination result of, merely, atypical cells or tissue in a tissue- or cell-level examination even though cancer is actually progressing. When it is not clearly differentiated whether the indeterminate tissue structure or cell morphology corresponds to an inflammatory lesion or a neoplasm, it is often diagnosed as atypism or cellular atypia. Therefore, several repeated re-examinations by another examination measure or the like are needed, and as a result, significant time and economic costs are consumed.

Various protein markers have been used to differentiate cancer cells in cytology, but outstanding usefulness has not been substantially obtained. As for p53 as an example, immunofluorescence using p53 was attempted in cytodiagnosis obtained through brush cytology in 1999. This assay showed a sensitivity of 43% (Tascilar M, Sturm P D, Caspers E, et al. Diagnostic p53 immunostaining of endobiliary brush cytology:preoperative cytology compared with the surgical specimen. Cancer 1999; 87:306-11), and another study subsequently reported that the assay showed lower sensitivity than conventional H&E staining (Stewart C J, Burke G M. Value of p53 immunostaining in pancreaticobiliary brush cytology specimens. Diagn. Cytopathol. 2000; 23:308-13). In addition, such an assay is known to have a limitation in that p53 is not expressed in 28.9% of bile duct cancer cells. As another example, an attempt was made to detect bile duct cancer through immunofluorescent staining using the fact that the minichromosome maintenance (MCM) replication proteins (Mcm2-7) are not expressed in malignant bile duct cancer, but results in a low sensitivity of 66% (Ayaru L, Stoeber K, Webster G J, et al. Diagnosis of pancreaticobiliary malignancy by detection of minichromosome maintenance protein 5 in bile aspirates. Br. J. Cancer 2008; 98:1548-54). As such, the previously known bile duct cancer molecule markers have limitations in that the markers show still low accuracy and reliability at the level of cytodiagnosis and thus do not exhibit substantial usefulness.

In spite of these studies and efforts with respect to the diagnosis of biliary tract cancer, there are neither effective markers nor pathological diagnostic methods that can accurately differentiate and determine malignant and benign states (bile duct diseases other than bile duct cancer) with high sensitivity and specificity merely through examination at the cellular level.

SUMMARY FO THE INVENTION

The present inventors, while studying a method capable of accurately diagnosing bile duct cancer at the cellular level, verified that the use of MRS as a marker in cytodiagnosis as well as biopsy showed almost 100% sensitivity and predictability in the definite diagnosis of a bile duct cancer, and in particular, accurately differentiated cancer cells from atypical cells, thereby completed the present invention.

Exemplary embodiments provide a method for treating a bile duct cancer in a latent patient, the method comprising the steps of:

obtaining a sample from a latent patient;

measuring the expression level of a methionyl-tRNA synthetase (MRS) protein in the sample;

comparing the measured protein expression level of the latent patient with that of a control;

diagnosing the patient with a bile duct cancer when the protein expression level of the patient is increased in comparison with that of the control; and treating the diagnosed patient by conducting at least one of a chemotherapy, a surgery, and a radiation therapy.

Another exemplary embodiments provide a method for improving sensitivity and specificity in cytodiagnosis or biopsy for a bile duct cancer, the method comprising the steps of:

(a) measuring the expression level of a methionyl-tRNA synthetase protein in a bile duct sample collected from a latent patient; and (b) determining that the patent is a bile duct cancer patient if the expression level of the methionyl-tRNA synthetase protein is increased in step (a).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Panel A shows the results confirming that MRS was strongly stained (detected) as a result of performing the MRS staining method of the present invention on the bile duct cells of a patient receiving a pathological finding of having bile duct cancer cells through a conventional staining method (Pap staining) and diagnosed with bile duct cancer in the final clinical pathological diagnosis.

Panel B shows the results confirming that MRS was strongly stained (detected) as a result of performing the MRS staining method of the present invention on the bile duct cells of a patient receiving a pathological finding of having cells suspected of bile duct cancer through a conventional staining method (Pap staining) and diagnosed with bile duct cancer in the final clinical pathological diagnosis.

Panel C shows the results confirming that MRS was strongly stained (detected) as a result of performing the MRS staining method of the present invention on the bile duct cells of a patient receiving a pathological finding of having atypical cells through a conventional staining method (Pap staining) and diagnosed with bile duct cancer in the final clinical pathological diagnosis.

Panel D shows the results confirming that MRS was not stained (detected) as a result of performing the MRS staining method of the present invention on the bile duct cells of a patient receiving a pathological finding of having atypical cells through a conventional staining method (Pap staining) and diagnosed as normal (benign bile duct strictures but not bile duct cancer) in the final clinical pathological diagnosis.

Panel E shows the results confirming that MRS was not stained (detected) as a result of performing the MRS staining method of the present invention on the bile duct cells of a patient receiving a pathological finding of having normal bile duct cells through a conventional staining method (Pap staining) and diagnosed as normal in the final clinical pathological diagnosis.

Figure 6:
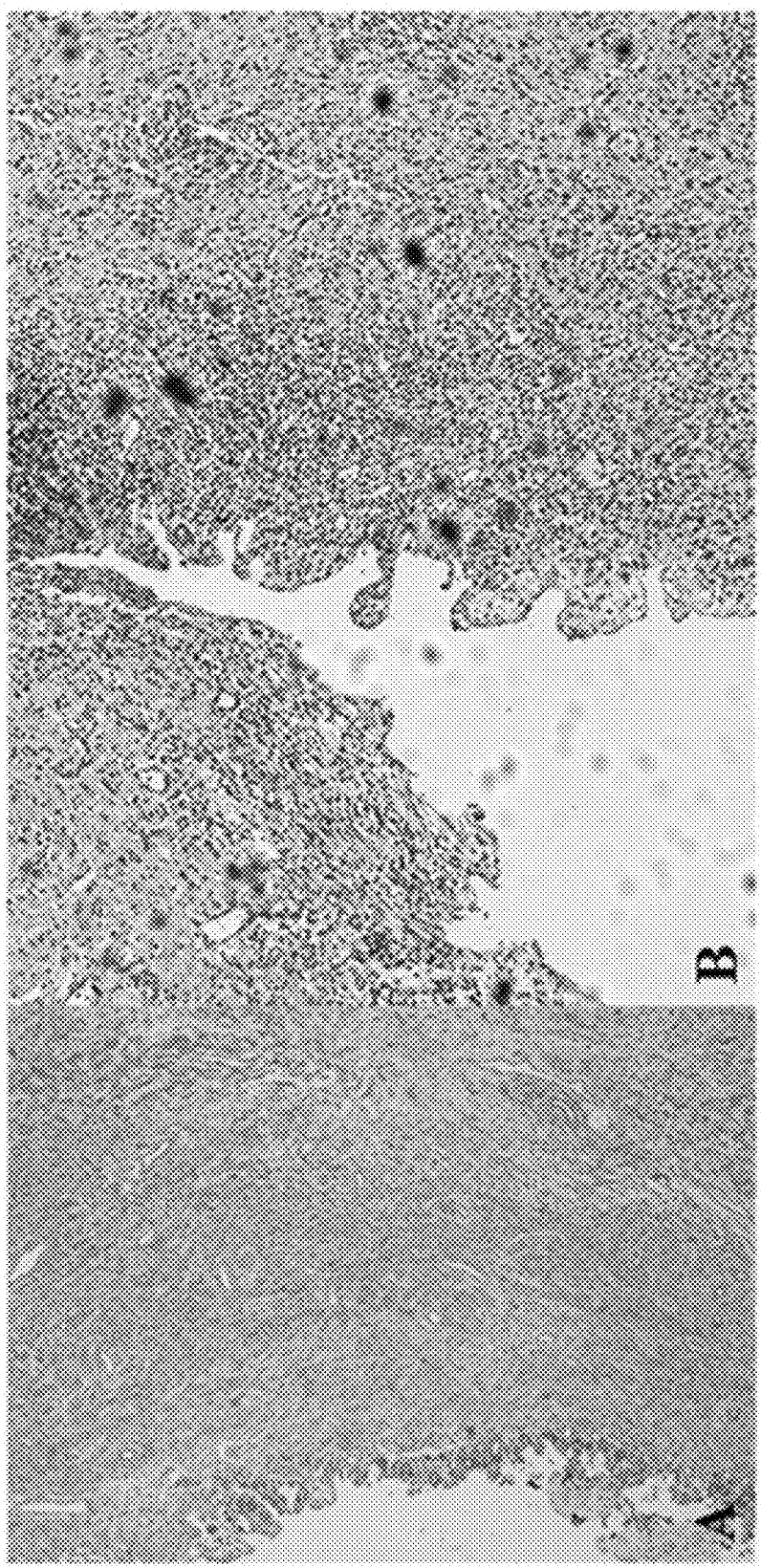

FIG. 6 shows the results confirming that MRS was not stained (detected) as a result of performing the MRS staining method of the present invention on the tissue determined to be normal bile duct tissue through H&E staining as a conventional staining method (panel A: H&E staining results (×100), panel B: results of MRS staining of the present invention (×100)).

Figure 7:
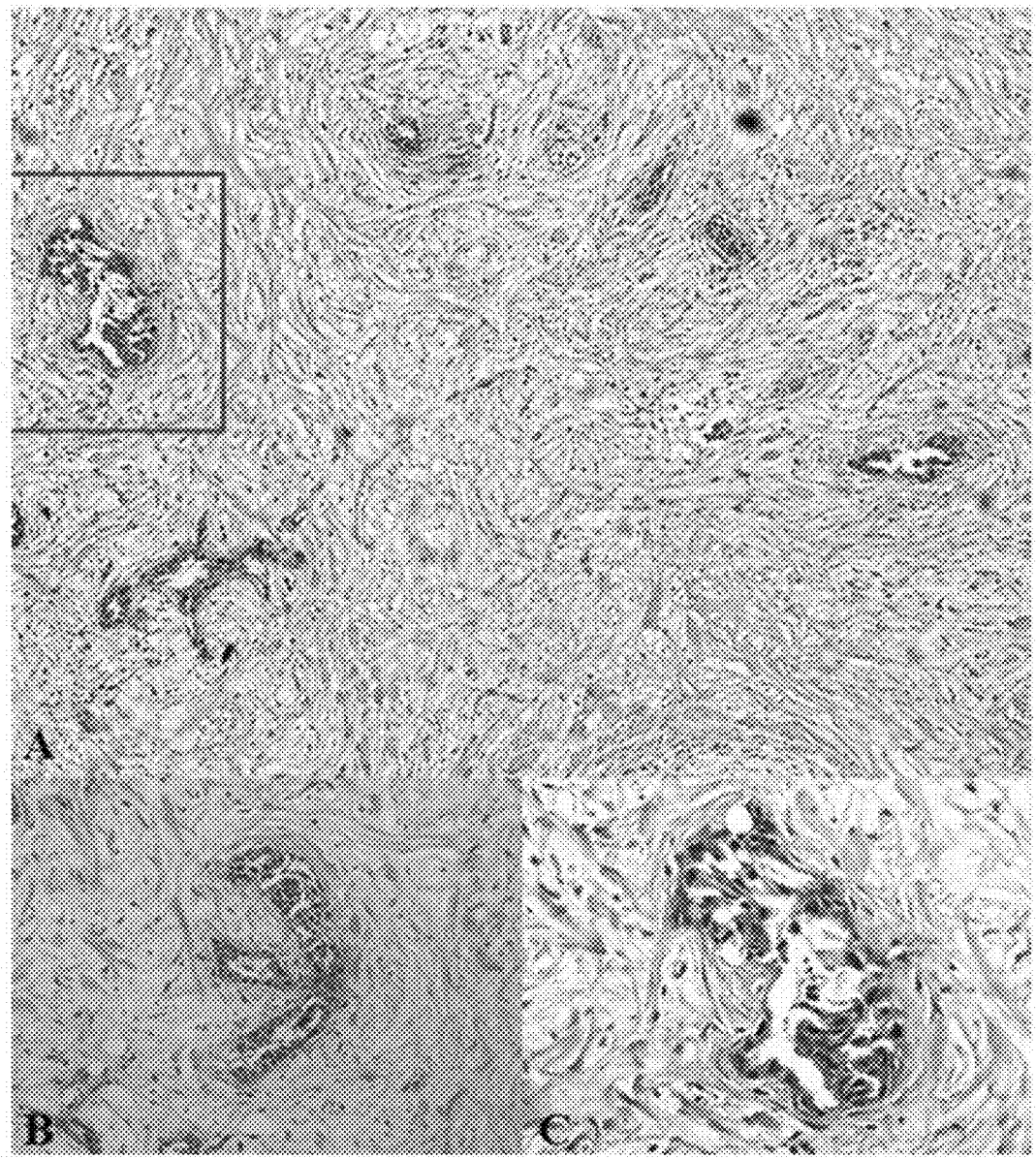

FIG. 7 shows the results confirming that MRS was strongly stained (detected) as a result of performing the MRS staining method of the present invention on the tissue determined to be bile duct cancer tissue through H&E staining as a conventional staining method (panel A: entire tissue specimen subjected to MRS staining of the present invention, panel B: H&E staining results (×100) corresponding to the red squared area in panel A, C: an enlargement (×100) of the red squared area in panel A).

Figure 8:
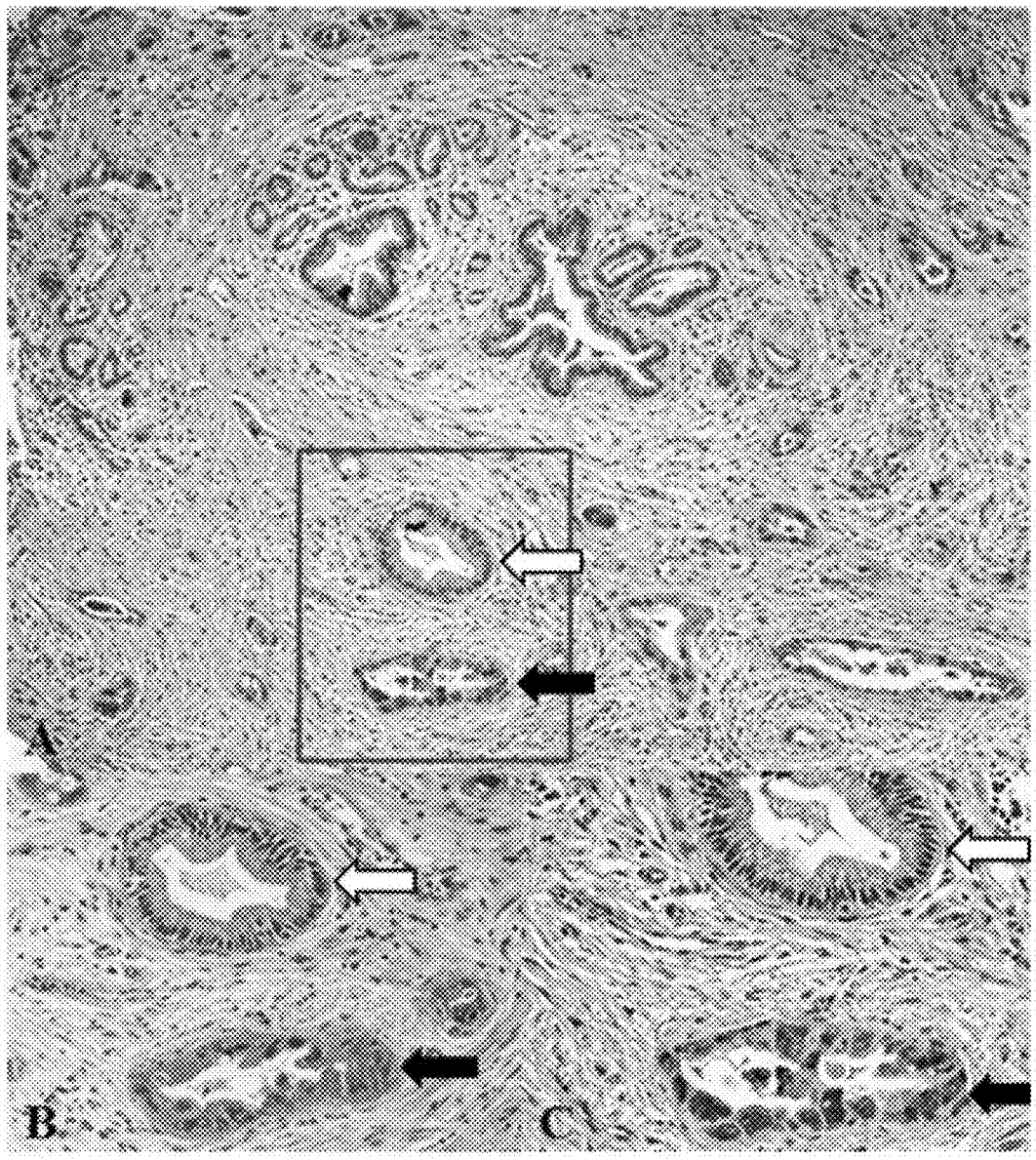

FIG. 8 comparatively shows the cancer tissue differentiating effect of the MRS staining method of the present invention in the tissue where bile duct cancer and normal bile duct tissue were co-present, wherein, through the MRS staining method (×100) of the present invention, strong staining (detection) results were shown only in the area determined to be bile duct cancer tissue through H&E staining as a conventional staining method, but no staining was shown in the normal bile duct tissue (panel A: entire tissue sample subjected to MRS staining of the present invention, panel B: H&E staining results (×100) corresponding to the red squared area in panel A, C: an enlargement (×100) of the red squared area in panel A, black arrows: bile duct cancer tissue, white arrows: normal bile duct tissue).

DETAILED DESCRIPTION OF THE ILLUSTRATED EMBODIMENTS

Hereinafter, the present invention will be described in detail.

The present invention provides a composition for diagnosing a bile duct cancer and a kit for diagnosing a bile duct cancer, wherein the composition and the kit each comprise an agent for measuring the expression level of a methionyl-tRNA synthetase (MRS) protein.

The present invention provides a composition for diagnosing bile duct cancer and a kit for diagnosing a bile duct cancer, wherein the composition and the kit each consist of an agent for measuring the expression level of a methionyl-tRNA synthetase (MRS) protein, respectively.

The present invention provides a composition for diagnosing bile duct cancer and a kit for diagnosing a bile duct cancer, wherein the composition and the kit each consist essentially of an agent for measuring the expression level of a methionyl-tRNA synthetase (MRS) protein, respectively.

Furthermore, the present invention provides use of an agent for measuring the expression level of a methionyl-tRNA synthetase (MRS) protein for preparing an agent for diagnosing bile duct cancer.

The present inventors first found that the expression level of MRS was specifically increased (overexpressed) in bile duct cancer cells or tissue. It was particularly found that MRS is very valuable as a diagnostic marker for bile duct cancer since only the measurement of an increase in MRS expression at the cellular level specifically differentiated a malignant state in patients with indeterminate bile duct stricture between malignant (bile duct cancer) and benign (normal compared with cancer) states, and especially, improved sensitivity and specificity of almost 100% for indeterminate cells, for which it is difficult to make a definite diagnosis of atypical cells through conventional cytodiagnosis pathology, thereby allowing a definite diagnosis on such cells. The use of MRS for diagnosis of bile duct cancer was first found by the present inventors, and the use of MRS for diagnosis of bile duct cancer on atypical cells or the use of MRS for differentiating (distinguishing) between cancer cells and normal cells in atypical cells is first disclosed in the present invention.

As used herein, the term "bile ducts" refers to all pathways through which bile is drained to the duodenum, and the term is interchangeable with "biliary tracts".

As used herein, the term "bile duct cancer" refers to a malignant neoplasm that has a fast proliferation rate, infiltrates into surrounding tissues, and metastasizes to other organs, including malignant tumors or cancer occurring in bile ducts. Malignant tumors or cancers are differentiated from benign tumors, which have a slow growth rate and do not metastasize.

Bile duct cancer as a target of diagnosis in the present invention is not particularly limited as to the cause thereof as long as a malignant neoplasm occurs in bile ducts (biliary tracts) regardless whether the bile duct cancer is primary cancer in the bile ducts or is caused by metastasis in the bile ducts. Preferably, primary cancer in the bile ducts may be a target of diagnosis.

As used herein, the term "normal" refers to a state of not being a malignant tumor or cancer (negative for malignancy), and the term is meant to encompass a completely normal state without any disease and a positive state for a (final) disease state determination corresponding to "benign". As used herein, the positive state corresponding to the term "benign" is distinguished from a positive indication denoted by "positive" through corresponding examination results, and the positive indication denoted by "positive" means that there is a response in the corresponding examination or there is a result indicating the possibility of cancer in the corresponding examination.

As used herein, the "MRS" refers to methionyl-tRNA synthetase, and the MRS is an enzyme that mediates an aminoacylation reaction of the amino acid methionine and tRNA. The MRS protein of the present invention is not particularly limited as to the sequence thereof as long as the MRS protein comprises a human or mammalian MRS amino acid sequence known in the art. For example, the human MRS protein is encoded by the MRS gene, and the MRS sequence information is known by a Genbank accession number, such as NM_004990 (mRNA), NP_004981.2, or P56192.2 (protein). Preferably, the MRS of the present invention may comprise the human MRS protein amino acid sequence defined by SEQ ID NO: 1. The MRS has two isoforms: a cytoplasmic form (cytoplasmic methionyl-tRNA synthetase); and a mitochondrial form (mitochondrial methionyl-tRNA synthetase). The MRS in the present invention may be preferably the cytoplasmic form.

As used herein, the term "expression" refers to the production of a protein or a nucleic acid in cells.

As used herein, the term "protein" is used interchangeably with the term "polypeptide" or "peptide", and refers to, for example, a polymer of amino acid residues, as is usually found in proteins in nature.

As used herein, the term "diagnosis" or "diagnosing" encompasses: determining the susceptibility of a subject to a particular disease or disorder; determining whether or not a subject currently has a particular disease or disorder; determining the prognosis of a subject with a specific disease or disorder (e.g., identification of pre-metastatic or metastatic cancer conditions, determination of cancer stages, or determination of responsiveness of cancer to treatment); or therametrics (e.g., monitoring states of a subject to provide information about treatment effects). The diagnosis in the present invention is identifying the presence or absence of bile duct cancer or the occurrence or non-occurrence thereof by determining the expression or non-expression of the MRS protein or the expression level thereof.

The agent for measuring the expression level of MRS protein is not particularly limited as to the kind thereof as long as the agent is known to be usable in the measurement of protein expression levels in the art. Preferably, the agent may be an antibody or an aptamer specifically binding to MRS protein.

As used herein, the term "antibody" refers to an immunoglobulin specifically binding to an antigenic site. More specifically, the term indicates a glycoprotein comprising at least two heavy (H) chains and at least two light (L) chains, which are held together by disulfide bonds. Each heavy chain is composed of a heavy chain variable region (abbreviated herein as HCVR or VH) and a heavy chain constant region. The heavy chain constant region is composed of three domains, CH1, CH2 and CH3. Each light chain is composed of a light chain variable region (abbreviated herein as LCVR or VL) and a light chain constant region. The light chain constant region is composed of one domain, CL. The VH and VL regions can be further subdivided into hypervariable regions (termed complementarity determining regions (CDRs)), with further conserved regions called framework regions (FRs) distributed therebetween. VH and VL each consist of three CDRs and four FRs, arranged from the amino-terminus to the carboxy-terminus in the following order: FR1, CDR1, FR2, CDR2, FR3, CDR3, and FR4. The variable regions of the heavy and light chains contain binding domains that interact with an antigen. The constant regions of an antibody may mediate the binding of an immunoglobulin to host tissues or factors, including various cells of the immune system (e.g., effector cells) and the first component (C1q) of the classical complement system.

The antibody in the present invention is an antibody that specifically binds only to MRS protein but does not respond to other proteins including different types of aminoacyl-tRNA synthetases. The antibody specifically binding to MRS protein in the present invention may be preferably an antibody specifically binding to a protein (MRS) containing the amino acid sequence of SEQ ID NO: 1. The MRS antibody may be produced by an ordinary method in the art: for example, MRS gene is cloned into an expression vector to obtain a protein encoded by the gene, and the protein thus obtained is injected into an animal to produce an antibody. The MRS antibody may be produced through the MRS full-length sequence protein. Alternatively, an MRS protein-specific antibody can be produced using an MRS protein fragment comprising an MRS antigenic site. The specific sequence and form of the antibody of the present invention are not particularly limited, and include a polyclonal antibody or a monoclonal antibody. In addition, the antibody is not particularly limited as to the type of immunoglobulin as provided, and for example, may be selected from the group consisting of IgG, IgA, IgM, IgE, and IgD, and may be preferably an IgG antibody. Furthermore, the antibody of the present invention includes special antibodies, such as a humanized antibody or a chimeric antibody, and recombinant antibodies as long as the antibody can specifically bind to MRS protein. In addition, a part of a whole antibody is also included in the antibody of the present invention as long as the part has antigen-antibody binding properties (response), and all types of immunoglobulin antibodies specifically binding to MRS are included in the antibody of the present invention. For example, the antibody of the present invention may include not only the full-form antibody having two full-length light chains and two full-length heavy chains but also functional fragments of the antibody molecule, that is, Fab, F(ab)2, Fab', F(ab')2, Fv, diabody, scFv, and the like, which have an antigen-binding function.

Fab (fragment antigen-binding) is an antigen-binding fragment of an antibody, and is composed of a heavy chain and a light chain each consisting of one variable domain and one constant domain. F(ab')$_2$ is a fragment produced by pepsin hydrolysis of an antibody, and F(ab')$_2$ has a form in which two Fab molecules are linked via disulfide bonds at the heavy-chain hinge region. F(ab') is a monomeric antibody fragment in which a heavy-chain hinge is added to a Fab separated from F(ab')$_2$ fragment by the reduction of disulfide bonds thereof. Fv (variable fragment) is an antibody fragment composed of only respective variable regions of a heavy chain and a light chain. scFv (single chain variable fragment) is a recombinant antibody fragment in which a heavy chain variable region (VH) and a light chain variable region (VL) are linked to each other via a flexible peptide linker. The term "diabody" refers to a fragment in which VH and VL of scFv, which cannot bind to each other due to the linkage thereof via a very short linker, bind to VL and VH of another scFv in the same form, respectively, to form a dimer. For the purpose of the present invention, the fragment of the antibody is not limited as to the structure or form thereof as long as the fragment of the antibody retains binding specificity to the human-derived MRS protein.

In the present invention, the antibody (including functional fragments thereof) is not particularly limited as to the site of MRS, with which the antibody interacts (that is, binds to) as long as the antibody can specifically bind to MRS protein, but preferably, the antibody may be an antibody or a functional fragment thereof, which specifically binds to an epitope region of MRS containing the amino acid sequence defined by SEQ ID NO: 20. More preferably, the antibody of the present invention may be an antibody or a fragment thereof, which specifically binds to an epitope comprising the 851nd to 880th amino acid resides in the methionyl-tRNA synthetase (MRS) protein defined by SEQ ID NO: 1.

In an example of the present invention, the present inventors verified that for high-sensitivity detection (staining) for MRS in bile duct cancer cells, an antibody having, as an epitope, a region of the amino acid sequence defined by SEQ ID NO: 20 in MRS was obtained, and that such an antibody could offer high-sensitivity detection ability for MRS.

The antibody specifically binding to an epitope region containing the amino acid sequence by SEQ ID NO: 20 is not particularly limited as to the specific sequence thereof as long as the antibody has desired specific binding ability, but preferably, the antibody may comprise:

a light chain variable region (VL) comprising: light chain complementarity-determining region 1 (CDR1) containing the amino acid sequence defined by SEQ ID NO: 2; a light chain complementarity-determining region 2 (CDR2) containing the amino acid sequence defined by SEQ ID NO: 4; and a light chain complementarity-determining region 3 (CDR3) containing the amino acid sequence defined by SEQ ID NO: 6, and a heavy chain variable region (VH) comprising: a heavy chain complementarity-determining region 1 (CDR1) containing the amino acid sequence defined by SEQ ID NO: 8; a heavy chain complementarity-determining region 2 (CDR2) containing the amino acid sequence defined by SEQ ID NO: 10; and a heavy chain complementarity-determining region 3 (CDR3) containing the amino acid sequence defined by SEQ ID NO: 12.

In the antibody (including fragments thereof) of the present invention, as a preferable example having the CDR configuration, the light chain variable region may comprise the amino acid sequence defined by SEQ ID NO: 14 and the heavy chain variable region may comprise the amino acid sequence defined by SEQ ID NO: 16.

As the most preferable example, the present invention provides an antibody composed of a light chain containing the amino acid sequence of SEQ ID NO: 18 and a heavy chain containing the amino acid sequence of SEQ ID NO: 19.

The antibody (including fragments thereof) of the present invention may, for "detection" thereof, be labeled with a general detectable moiety. For example, the antibody may be labeled with a radioisotope or fluorescent label by using the technique described in the literature [Current Protocols in Immunology, Volumes 1 and 2, 1991, Coligen, et al., Ed. Wiley-Interscience, New York, N.Y., Pubs]. In addition, various enzyme-substrate labels are usable, and examples of enzymatic labels include: luciferase, such as drosophila luciferase and bacterial luciferase (U.S. Pat. No. 4,737,456), luciferin, 2,3-dihydrophthalazinedionese, malate dehydrogenase, urease, peroxidase such as horseradish peroxidase (HRPO), alkaline phosphatase, β-galactosidase, glucoamylase, lysozyme, saccharide oxidase (e.g., glucose oxidase, galactose oxidase, and glucose-6-phosphate dehydrogenase), heterocyclic oxidase (e.g., uricase and xanthine oxidase), lactoperoxidase, microperoxidase, and the like. Techniques for conjugating an enzyme to an antibody are disclosed in the literature [O'Sullivan et al., 1981, Methods for the Preparation of Enzyme-Antibody Conjugates for use in Enzyme Immunoassay, in Methods in Enzym. (J. Langone& H. Van Vunakis, eds.), Academic press, N.Y., 73: 147-166]. The labels may be directly or indirectly conjugated to antibodies using various known techniques. For example, an antibody may be conjugated to biotin, and any labels pertaining to three classes of widespread categories cited above may be conjugated to avidin or vice versa. Biotin may selectively bind to avidin, and therefore, this label may be conjugated to an antibody in such an indirect manner. Alternatively, in order to attain the indirect conjugation of a label to an antibody, the antibody may be conjugated to a small hapten (e.g., digoxin), and one of the different types of labels set forth above may be conjugated to an anti-hapten antibody (e.g., an anti-digoxin antibody). Therefore, the indirect conjugation of labels to antibodies can be attained.

As used herein, the term "aptamer" refers to a substance capable of specifically binding to an analyte to be detected in a sample, wherein the aptamer means a single-stranded nucleic acid having a stable three-dimensional structure per se (DNA, RNA, or a modified nucleic acid), and the presence of a target protein in a sample can be specifically identified by the aptamer. The aptamer may be prepared according to an ordinary aptamer preparation method by determining and synthesizing a sequence of an oligonucleotide having selectivity and high binding ability to a target protein to be identified and then modifying the 5'-terminus or 3'-terminus of the oligonucleotide to have —SH, —COOH, —OH, or —NH2 so as to bind the 5'-terminus or 3'-terminus to a functional group of an aptamer chip, but is not limited thereto.

The kit for diagnosing bile duct cancer of the present invention may comprise not only an antibody or aptamer selectively recognizing MRS protein as a marker to measure the expression level of MRS but also one or more kinds of other constituent compositions, solutions, or devices suitable for analysis. In a specific aspect, the kit may be a diagnostic kit comprising known essential elements and subsidiary elements needed for performing Western blotting, ELISA, radioimmunoassay, radioimmunodiffusion, Ouchterlony immunodiffusion, rocket immunoelectrophoresis, immunohistostaining assay, immunoprecipitation assay, complement fixation assay, FACS, or protein chip assay, but is not limited thereto.

For example, the kit may comprise an antibody specific to an MRS marker protein. The antibody may be a monoclonal, polyclonal, or recombinant antibody, which has high specificity and affinity to an MRS marker protein and has little cross-activity to other proteins. In addition, the kit may comprise an antibody specific to a control protein. The antibody provided in the kit may itself be labeled with a detectable moiety, which is as described above. Additionally, the kit may further comprise separate reagents capable of detecting bound antibodies, for example, a labeled secondary antibody, a chromophore, an enzyme (e.g., in the form of being conjugated with the antibody) and a substrate thereof, or other materials capable of binding to the antibody. In addition, the kit of the present invention may comprise a wash or an eluent, which can remove excess chromogenic substrate, unbound proteins, and the like but retain only a protein marker binding to an antibody.

The agent for measuring the expression level of MRS protein may also be meant to include an agent for detecting MRS mRNA. An increase in the expression level of a protein is accompanied by an increase in transcripts (e.g., mRNA) from a gene encoding the protein, and therefore a person skilled in the art could obviously understand that not only a means of detecting the MRS protein itself but also a means of indirectly detecting transcripts directly related to the expression of MRS protein can be used.

The agent for detecting MRS mRNA is not particularly limited as to the type thereof as long as the agent is a ligand specifically binding to or hybridizing with MRS mRNA, but may be, for example, a primer (pair) or a probe.

The term "primer" refers to a short nucleic acid sequence having a short free 3' hydroxyl group, wherein the nucleic acid sequence can form base pairs with a complementary template and act as a starting point for template strand replication. Primers may initiate DNA synthesis in the presence of reagents for polymerization (i.e., DNA polymerase or reverse transcriptase) and four different nucleoside triphosphates in conditions of appropriate buffer and temperature conditions. The PCR conditions, and the length of sense and antisense primers can be appropriately selected according to a technique known in the art.

The sequence of the primer does not necessarily need to be perfectly complementary to the sequences of some nucleotides in the template, and the primer is sufficient as long as the primer hybridizes with the template to have sufficient complementarity within a range in which the primer can perform its inherent actions. Therefore, primers for measuring the expression level of MRS mRNA in the present invention do not necessarily need to be perfectly complementary to the MRS coding gene sequence, and the primers are sufficient as long as the primers have a length and complementarity that are fit for the purpose of measuring the amount of MRS mRNA by amplifying a specific section of MRS mRNA or MRS cDNA through DNS synthesis. Primers for the amplification consist of one set (or pair) of primers that bind complementarily to a template (or sense) and an opposite side (antisense), respectively, at both ends of a specific region of the MRS mRNA to be amplified. A person skilled in the art could easily design the primers with reference to the nucleotide sequence of MRS mRNA or cDNA.

The term "probe" refers to a fragment of a polynucleotide, such as RNA or DNA, capable of specifically binding to mRNA or complementary DNA (cDNA) of a specific gene and having a length from several to several hundreds of base pairs. Since the probe is labeled, the probe can be used to check the presence or absence of target mRNA or cDNA to be bound or the expression level thereof. For the purpose of the present invention, the probe complementary to MRS mRNA can be used for the diagnosis of Alzheimer's disease by measuring the expression level of MRS mRNA through hybridization with a sample of a subject. The selection and hybridization conditions of probes may be appropriately selected according to a technique known in the art.

The primers or probes of the present invention may be chemically synthesized using phosphoramidite solid support synthesis or other well-known methods. In addition, the primers or probes may be variously modified by a method known in the art within the scope within which hybridization with MRS mRNA is not impeded. Examples of the modification are methylation, capping, substitution of at least one natural nucleotide with an analogue thereof, and modification between nucleotides, for example, modification with an uncharged linker (e. g., methyl phosphonate, phosphotriester, phosphoramidate, carbamate, etc.) or a charged linker (e. g., phosphorothioate, phosphorodithioate, etc.), and binding with a labeling material using a fluorescence or an enzyme.

The diagnostic kit of the present invention may comprise not only primers or probes recognizing MRS protein to measure the expression level of MRS but also one or more kinds of other constituent compositions, solutions, or devices suitable for analysis. The kit is not particularly limited as to the kind thereof as long as the kit is a known diagnostic kit providing primers (primer pairs) or probe as constituents. For example, the kit may include a kit for polymerase chain reaction (PCR), RNase protection assay, northern blotting, southern blotting, or a DNA microarray chip.

As an example, the diagnostic kit may be a kit for diagnosis comprising essential elements required to perform PCR. A PCR kit comprises respective primer pairs specific to marker genes (mRNA). The primers are nucleotides having sequences specific to each marker gene (mRNA), and have a length of about 7-30 bp, and more preferably, about 10-23 bp. In addition, the PCR kit may comprise primers specific to the nucleic acid sequence of a control gene. Besides, the PCR kit may comprise test tubes or appropriate containers, buffers (varying in pH and magnesium concentration), deoxynucleotides (dNTPs), DNA polymerase (e.g., Taq-polymerase) and reverse transcriptase, DNAse and RNAse inhibitors, DEPC-water, sterilized water, and the like.

As used herein, the term "comprising" is used synonymously with "containing" or "characterized by", and does not exclude additional ingredients or steps not mentioned in the composition or method. The term "consisting of" is used in the same manner as "composed of", and is meant to exclude additional elements, steps, or ingredients that are not separately described. The term "essentially consisting of" is meant to encompass the mentioned elements or steps as well as any element or step that does not substantially affect the basic characteristics of the mentioned elements or steps in the ranges of compositions or methods.

The present invention provides a method for diagnosing bile duct cancer, wherein the expression level of a methionyl-tRNA synthetase (MRS) protein in a sample from a subject is measured.

The subject of the present invention may be an animal, preferably a mammal, particularly an animal including a human being, and more preferably a human or a patient in need of diagnosis. The subject will be described later in more detail.

Specifically, the present invention provides a method for qualitatively or quantitatively analyzing a methionyl-tRNA synthetase protein in a bile duct sample collected from a latent patient in order to provide information necessary for diagnosis of bile duct cancer.

Specifically, the method may comprise:

(a) measuring the expression level of the methionyl-tRNA synthetase protein in the bile duct sample collected from a latent patient; and (b) determining that the patient is a bile duct cancer patient if the expression level of the methionyl-tRNA synthetase protein is increased in step (a).

As used herein, the term "analysis" refers preferably to "measurement", and in the present invention, the analysis or measurement can be performed without limitation, and the term includes both qualitative and quantitative methods. In the measurement at the protein level, the kinds of qualitative and quantitative methods are well known in the art, in which the test methods described herein are included. Specific comparisons at the protein level between the respective methods are well known in the art.

The present inventors are the first to find that MRS can function as a diagnostic marker for bile duct cancer. Especially, MRS has an excellent effect of diagnosing bile duct cancer, as a marker for cytodiagnosis. Therefore, the present invention provides a method for providing information necessary for diagnosis of bile duct cancer by measuring the expression level of MRS. Hereinafter, the method of the present invention will be described stepwise.

In step (a), the bile duct sample collected from a latent patient is provided, and the expression level of the methionyl-tRNA synthetase protein is measured in the sample.

The sample is not particularly limited as long as the sample is collected from an object (patient) or a subject to be diagnosed for the presence or absence of bile duct cancer; however, for example, the sample may be bile duct tissue or bile duct cells. Specifically, the sample may be bile duct tissue or cells obtained from bile ducts by biopsy, or bile duct cells obtained from bile ducts by fine needle aspiration, brush cytology, or bile aspiration. Most preferably, the sample may be bile duct cells obtained by brushing cytology.

In one preferable embodiment, epithelial cells apparently derived from bile ducts need to be present in the bile duct cell sample.

The obtained bile duct cells or tissue may be provided by pretreatment according to a typical sample pretreatment manner (e.g., fixation, centrifugation, smearing on slides, etc.) known in the art. In one preferable embodiment, the bile duct cell sample may be prepared by pretreatment through a typical liquid-based monolayer slide preparation method (a method for preparing a slide for liquid-based cytology). For example, the bile duct cell sample may be provided on a test slide by a liquid-based monolayer attachment method using ThinPrep, SurePath, CellPrep, or the like.

As used herein, the term "collection by brush cytology" refers to a manner in which cells are collected by brushing the surface of bile ducts (especially, an area suspected of being diseased) using a typical cytology brush, and the term can be interchangeably used herein with names commonly used in the art, such as brushing cytology.

As used herein, the term "latent patient" refers to a patient suspected of a bile duct cancer, and means a patient suspected of having bile duct cancer through various examinations, such as clinical symptoms, hematological examinations, or imaging examinations.

That is, the latent patient includes a patient who can or cannot be diagnosed with bile duct cancer through imaging examinations, and also means a patient who is suspected of bile duct cancer due to clinical symptoms or through hematological examinations even though the patient cannot be diagnosed with bile duct cancer through imaging examinations. The clinical symptoms that may occur in bile duct cancer patients include abdominal pain, jaundice, and weight loss, but these symptoms are not specific only to bile duct cancer. In addition, the level of jaundice or diabetes or tumor markers, such as CEA, CA19-9, may be increased in hematological examinations, but these data are not observed in all patients suspected of bile duct cancer. Imaging examinations may be performed by abdominal ultrasound, abdominal endoscopic ultrasound, abdominal CT, abdominal MRI, or PET-CT. These imaging examinations comparatively easily make suspicion of cancer when bile duct cancer is present in a mass-forming type, but a diagnosis of bile duct cancer is difficult to make through only the imaging examinations if the bile duct cancer is present in a periductal-infiltrating type or an intraductal-growing type and is accompanied by bile duct strictures or the like. Imaging examinations alone cannot make a definite diagnosis of bile duct cancer. The final definite diagnosis of bile duct cancer is performed through pathological examinations, wherein the definite diagnosis is made by observing tissue obtained after surgery on operable patients and through biopsy or cytodiagnosis in the case of inoperable patients.

Preferably, the latent patient may mean a patient who has general symptoms, such as abdominal pain, jaundice, and weight loss, generally observed in bile duct cancer, but cannot be definitively diagnosed with bile duct cancer through imaging diagnostic apparatuses, such as CT, ultrasound, and MRI. More preferably, the latent patient may be a patient who cannot undergo an invasive biopsy of a large area, wherein the patient may be a patient in need of clear diagnosis with respect to bile duct cancer dependent on cytology (cytodiagnosis). That is, the latent patient may be a patient in need of clear diagnosis with respect to bile duct cancer through cytological analysis since the patient cannot undergo surgery and thus cannot receive a bile duct biopsy or cannot receive a bile duct biopsy due to complications and other causes, but is not limited thereto.

The measuring of the expression level of MRS protein means measuring expression or non-expression (that is, measuring the presence or absence of expression) or qualitatively or quantitatively measuring the level of change of the protein.

As used herein, the term "increase of expression" of MRS protein means that a previously unexpressed one is expressed (that is, a previously undetected one is detected) or there is an overexpression relative to a normal level (that is, the detected amount of is increased).

For example, the expression level of MRS protein may be detected or measured using an antibody specifically binding to MRS protein, but is not limited thereto. The antibody specifically binding to MRS protein in the present invention is as described above. The method for measuring the expression level of MRS protein is not particularly limited as long as the method is a method known in the art, but may use, for example, any one of western blotting, enzyme-linked immunosorbent assay (ELISA), radioimmunoassay, radioimmunodiffusion, Ouchterlony immunodiffusion, rocket immunoelectrophoresis, immunostaining (including immunohistochemistry staining, immunocytochemistry staining, and immunofluorescent staining), immunoprecipitation assay, complement fixation assay, FACS, or protein chip assay. Besides, the measurement method is understood in accordance with the above description of the agent for measuring the expression level of MRS and the kit comprising the same, which are provided in the present invention.

Conventionally reported diagnostic markers for bile duct cancer fail to attain effective diagnosis when applied to cytodiagnosis since such diagnostic markers had poor sensitivity and specificity in diagnosis at the cellular level unlike when applied to biopsy. Moreover, as for conventional cytodiagnosis results for patients with bile duct strictures, it is difficult to determine whether the patients have bile duct cancer or other benign bile duct disease. That is, conventional cytodiagnosis often makes a pathological finding of atypical cells without clearly indicating whether the cells are bile duct cancer cells or normal cells (including benign disease cells but not bile duct cancer), and such cases require additional and multiple repetitive re-examinations.

In contrast, the use of MRS according to the present invention shows sensitivity and specificity at 100% even when applied to cytodiagnosis, leading to excellent accuracy in diagnosis, thereby allowing definite diagnosis of bile duct cancer through cytodiagnosis alone and, especially, provides a great advantage in differentiating bile duct cancer cells and normal cells in patients with bile duct strictures. In conventional cytodiagnosis performed on the patient found to have bile duct strictures, the cells are often determined to be atypical, resulting in undiagnosable cells. However, the use of MRS according to the present invention enables a clear determination, at the level of bile duct cells, as to whether the cells are tumor cells, thereby enabling more accurate diagnosis of bile duct cancer. It is very difficult to differentiate whether atypical cells correspond to a tumor or other benign disease, such as cholangitis, through H&E staining or pap staining, which is generally used to diagnose cancer. Therefore, it is clinically very important to determine whether atypical cells correspond to a malignant tumor, and the use of MRS according to the present invention is very meaningful that atypical cells can be determined to be malignant tumor cells when a (high) expression of MRS is observed in the atypical cells. Considering that a biopsy requiring biotomy aggravates the physical burden on patients more than cytodiagnosis in view of sample acquisition, the present invention providing accurate diagnosis at the cellular level has yet greater advantage.

In the present invention, the morphological diagnosis-typed pathological examination, which has been conventionally used, may be performed before, simultaneously with, or after step (a). That is, steps (i) and (ii) below may be further performed before, simultaneously with, or after step (a):

(i) staining the bile duct cells collected from the latent patient with: at least one nucleus-staining solution selected from the group consisting of 4',6-diamidino-2-phenylindole (DAPI), methylene blue, acetocarmine, toluidine blue, hematoxylin, and Hoechst; and at least one cytoplasm-staining solution selected from the group consisting of eosin, crystal violet, and Orange G; and (ii) determining by said cell staining that the bile duct cells are malignant tumor cells, atypical cells, or normal cells.

The malignant tumor cells determined in step (ii) may include, without limitation thereto, specifically, cells determined to be "suspicious of malignancy" and "positive for malignancy" in the morphological diagnosis-typed pathological examination.

As used herein, the term "morphological diagnosis-typed pathological examination" or "morphological examination" refers to examination of an abnormal morphological change when normal cells are transformed into cancer. Specific examination items or their criteria with respect to the abnormal morphological change are not particularly limited as long as the abnormal morphological change is a kind of morphological change of cancer cells in the art, but at least one selected from the group consisting of: cell clustering; the nucleus/cytoplasm ratio (N/C ratio); the shape of the nuclear membrane (irregularity of the nuclear membrane shape); chromatin agglomeration; an appearance of nucleoli in the nucleus; and an appearance of mitosis may be examined. The morphological examination may be performed simultaneously with, separately from, or sequentially with the foregoing method for providing information necessary for the diagnosis of bile duct cancer, the method comprising steps (a) to (b).

In step (ii), the determining of the bile duct cells to be malignant tumor cells, atypical cells, or normal cells from the cell-staining results in step (i) may be made on the basis of abnormal morphological changes when normal cells are transformed into cancer, and the specific determination criteria are well known in the art. The "atypical cells" means cells that cannot be clearly determined to be malignant tumor cells (cancer cells) or normal cells by a morphological change.

In one preferable embodiment of the present invention, in step (ii), the determining of the bile duct cells to be malignant tumor cells, atypical cells, or normal cells from the cell-staining results in step (i) may be performed according to the following criteria:

the bile duct cells are determined to be malignant cells when there are two or more types of morphological abnormality selected from the group consisting of: three-dimensional smear of cells; a high nucleus/cytoplasm ratio (N/C ratio); an appearance of chromatin agglomeration; a rough-shaped nuclear membrane (an increased irregularity of the nuclear membrane); an appearance of nucleoli; and an appearance of mitosis;

the bile duct cells are determined to be normal cells when the cells are smeared in one layer; the nucleus/cytoplasm ratio (N/C ratio) is small; and the nuclear membrane has a smooth shape; and the bile duct cells are determined to be atypical cells (including benign) when the cell change does not reach malignant cells but can be diagnosed to be normal.

Diagnostic results with very high accuracy can be obtained merely through examination at the cellular level (that is, cytodiagnosis) when steps (i) and (ii) are performed in parallel before, simultaneously with, or after step (a). For example, in cases where the steps are performed before step (a), the bile duct cells determined to be tumor cells or normal cells through cell staining can be determined more accurately as bile duct cancer cells or normal cells by additionally re-analyzing the expression level (presence or absence) of MRS in step (a), which is subsequently performed, and thus errors in diagnosis can be significantly reduced. In cases where the bile duct cells are determined to be atypical cells through cell staining, the bile duct cells can be clearly determined to be tumor cells or non-tumor cells by analyzing the expression level (presence or absence) of MRS in step (a), which is subsequently performed. As such, a definite diagnosis with high accuracy can be made at the cellular level, thereby dramatically solving problems with conventional pathological examinations, for example, the trouble of repeatedly performing a biopsy and then re-diagnosis upon receipt of examination results indicating atypical cells, and the physical burden on a patient attributable to the need for three or more tissue sample for accurate confirmation of bile duct cancer from a biopsy tissue sample, leading to a very excellent diagnostic effect.

In step (b), the patient, from which the corresponding bile duct sample was collected, is determined to be bile duct cancer patient if the expression level of MRS is increased in the bile duct sample measurement in step (a).

In step (b), the extent of increase in MRS expression level, which is a criterion for the diagnosis of bile duct cancer, can be determined by the presence or absence of expression or the grades of expression according to the measurement method used in the art. For example, a normal range, a bile duct cancer occurrence range, and the like are classified according to the degree of MRS expression level by measuring the expression levels of MRS in samples of multiple normal persons and patients, followed by data storage and analysis, so that an appropriate criterion for diagnosis can be provided.

Step (b) may be performed in comparison with a control (negative control), and the control is meant to include all of normal bile duct samples from subjects to be tested (that is, identical latent patients) or bile duct samples from other normal subjects (bile duct cancer-free subjects). In addition, the control may be clearly described in the agent for measuring MRS expression levels or the kit comprising the same, which are provide in the present invention, or the control may be provided incidentally. Compared with such a control, the high level of MRS expression level in a sample of a target subject can be determined to indicate a bile duct cancer patient.

In addition, the present invention can provide a method for differentiating between cancer cells and tumor cells in atypical cells by comprising steps (a) and (b).

As used herein, the term "sensitivity" refers to a rate of the diagnosis of bile duct cancer made through a target examination (e.g., an examination of the present invention) for a sample or patient having a final clinical pathological diagnosis of bile duct cancer.

As used herein, the term "specificity" refers to a rate of the diagnosis of being normal made through a target examination (e.g., an examination of the present invention) for a sample or patient having a final clinical pathological diagnosis of being normal.

When a diagnosis of bile duct cancer is made by using MRS as a marker and detecting the increase thereof, the result is almost 100% sensitivity and specificity in diagnosis at the tissue and cellular levels.

Specifically, the sensitivity and specificity are 90% or higher (90-100%, preferably 90-99%, and more preferably 90-98%).

Preferably, the sensitivity and specificity are 95% or higher (95-100%, preferably 95-99%, and more preferably 95-98%).

Furthermore, the present invention provides a method for improving sensitivity and specificity in cytodiagnosis or biopsy for bile duct cells, the method comprising the steps of:

(a) measuring the expression level of a methionyl-tRNA synthetase protein in a bile duct sample collected from a latent patient; and (b) determining that the patient is a bile duct cancer patient if the expression level of the methionyl-tRNA synthetase protein is increased in step (a).

It would be obvious to a person skilled in the art that an improvement in sensitivity and specificity leads to an improvement in accuracy in diagnosis. Therefore, the method of the present invention may be understood as a method for improving accuracy in diagnosis, and the accuracy may reach a level of 90-100%, more preferably 90-99%, still more preferably 93-98%, and most preferably 95-98%.

Furthermore, the present invention provides a method for providing information necessary for diagnosis of bile duct cancer in cytodignosis or biopsy for bile duct cancer, wherein adjuvant method is performed in combination with a morphological examination, the adjuvant method comprising:

(a) measuring the expression level of a methionyl-tRNA synthetase protein in a bile duct sample collected from a latent patient; and (b) determining that the patient is a bile duct cancer patient if the expression level of the methionyl-tRNA synthetase protein is increased in step (a).

The morphological examination is meant to include, as a preferable example, an examination conducted by comprising the foregoing steps (i) and (ii), and include other morphological examinations in accordance with such a manner. The description thereof will be made with reference to the above details, and a person skilled in the art could use the above manner through appropriate selection.

The specific description of steps (a) and (b) are as described above, and the steps may be performed simultaneously with, separately from, or sequentially with the morphological examination when such steps are performed adjunctively (i.e., as an adjuvant therapy). In addition, the adjuvant therapy comprising steps (a) and (b) may be performed before, simultaneously with, or after the morphological examination.

Furthermore, the present invention provides a method for treating a bile duct cancer in a latent patient, the method comprising the steps of:

obtaining a sample from a latent patient;

measuring the expression level of a methionyl-tRNA synthetase (MRS) protein in the sample;

comparing the measured protein expression level of the latent patient with that of a control;

diagnosing the patient with a bile duct cancer when the protein expression level of the patient is increased in comparison with that of the control; and treating the diagnosed patient by conducting at least one of a chemotherapy, a surgery, and a radiation therapy.

According to exemplary embodiments of the present invention, the methionyl-tRNA synthetase protein contains the amino acid sequence defined by SEQ ID NO: 1.

According to exemplary embodiments of the present invention, the step of measuring is conducted by an agent which comprises an antibody or aptamer specifically binding to the methionyl-tRNA synthetase (MRS) protein.

According to exemplary embodiments of the present invention, the step of diagnosing is conducted by a kit which comprises an agent for measuring the expression level of a methionyl-tRNA synthetase (MRS) protein.

According to exemplary embodiments of the present invention, the sample is bile duct cells.

According to exemplary embodiments of the present invention, the method further comprises the following steps before, simultaneously with, or after the step of measuring:

(i) staining the bile duct cells with: at least one nucleus-staining solution selected from the group consisting of 4',6-diamidino-2-phenylindole (DAPI), methylene blue, acetocarmine, toluidine blue, hematoxylin, and Hoechst, and at least one cytoplasm-staining solution selected from the group consisting of eosin, crystal violet, and Orange G; and (ii) determining by said cell staining that the bile duct cells are malignant tumor cells, atypical cells, or normal cells.

According to exemplary embodiments of the present invention, in step (ii), it is determined by cell-staining results of step (i) that:

the bile duct cells are malignant cells when there are two or more types of morphological abnormality selected from the group consisting of: three-dimensional smear of cells, a high nucleus/cytoplasm ratio (N/C ratio), an appearance of chromatin agglomeration; a rough-shaped nuclear membrane, an appearance of nucleoli, and an appearance of mitosis;

the bile duct cells are normal cells when the cells are smeared in one layer, the nucleus/cytoplasm ratio (N/C ratio) is low, and the nuclear membrane has a smooth shape; and the bile duct cells are atypical cells when the extent of a cell change does not reach that of malignant cells but cannot be diagnosed as normal.

According to exemplary embodiments of the present invention, the bile duct cells are collected by brush cytology.

According to exemplary embodiments of the present invention, the expression level of the protein is measured using any one of Western blotting, ELISA, radioimmunoassay, radioimmunodiffusion, Ouchterlony immunodiffusion, rocket immunoelectrophoresis, immunostaining, immunoprecipitation assay, complement fixation assay, FACS, or protein chip assay.

According to exemplary embodiments of the present invention, the antibody is an antibody or a functional fragment thereof, which specifically binds to an epitope region of MRS containing the amino acid sequence defined by SEQ ID NO: 20.

According to exemplary embodiments of the present invention, wherein the antibody comprises:

a light chain variable region (VL) containing the amino acid sequence defined by SEQ ID NO: 14; and a heavy chain variable region (VH) containing the amino acid sequence defined by SEQ ID NO: 16.

According to exemplary embodiments of the present invention, the step of measuring is conducted by an agent which comprises a primer or probe specifically binding to the methionyl-tRNA synthetase mRNA.

Furthermore, the present invention provides a method for improving sensitivity and specificity in cytodiagnosis or biopsy for a bile duct cancer, the method comprising the steps of:

(a) measuring the expression level of a methionyl-tRNA synthetase protein in a bile duct sample collected from a latent patient; and (b) determining that the patient is a bile duct cancer patient if the expression level of the methionyl-tRNA synthetase protein is increased in step (a).

According to exemplary embodiments of the present invention, the sensitivity and specificity are 90% or higher.

According to exemplary embodiments of the present invention, the cytodiagnosis is brush cytology.

According to exemplary embodiments of the present invention, the steps of (a) measuring and (b) determining are performed simultaneously with, separately from, or sequentially with a morphological examination.

According to exemplary embodiments of the present invention, the morphological examination is performed by examining at least one selected from the group consisting of cell clustering, the nucleus/cytoplasm ratio (N/C ratio), the shape of the nuclear membrane, chromatin agglomeration, an appearance of nucleoli in a nucleus, and an appearance of mitosis.

MRS is overexpressed only for bile duct cancer, as differentiating between normal cells and other benign bile duct diseases, and the use of MRS can attain a definite diagnosis of bile duct cancer with almost 100% sensitivity, specificity, and accuracy for even indeterminate atypical cells determined through conventional cytodiagnosis pathology, and thus MRS is valuable as a diagnostic maker for bile duct cancer. Therefore, the present invention provides a method for differentiating between cancer cells and normal cells in atypical cells, and according to the present invention, a definite diagnosis of cancer can be made with almost 100% sensitivity, specificity, and accuracy, in contrast with many conventional cancer markers, with which an effective diagnosis is substantially difficult to obtain at the cellular level (that is, cytodiagnosis).

The following examples are merely for illustrating the present invention, and are not intended to limit the scope of the present invention.

Example 1

Construction of Useful Antibody for Bile Duct Cancer Examination of Present Invention (Obtaining Antibody Having High Specificity to MRS)

It is known that, in vivo, methionyl-tRNA synthetase (MRS) is present in a state of binding with aminoacyl-tRNA synthetase complex-interacting multifunctional protein 3 (AIMP3), and such binding is broken by UV irradiation or the like. Therefore, for substantial accurate detection of MRS, only MRS needs to be specifically detected, even in situations where MRS binds with AIMP3. However, current AIMP types and ARS types have many similarities in protein structure therebetween, and thus commercial antibodies have a problem of showing cross-activity with different AIMP and ARS types. For diagnostic accuracy of the examination method for bile duct cancer of the present invention, the present inventors produced high-sensitivity MRS antibody having no cross-activity with the other proteins as below.

<1-1> Production of MRS-AIMP3 Protein

MRS-AIMP3 co-purified protein was expressed and purified on *E. coli*, and specific experiment methods are as follows. BL21DE3 strain was transformed so as to express MRS (SEQ ID: 1) and AIMP3 (SEQ ID NO: 21, NCBI ref. NM_004280.4) and cultured in LB medium, and then single colonies were cultured to reach an OD600 value of 0.6-0.8 in 5 ml of LB liquid medium containing ampicillin. After 1 mM IPTG was added, the cells were incubated at 37° C. for 3 hours, and then only the cells were obtained by centrifugation for 10 minutes. SDS-PAGE was performed on the cell liquid, and the expression of the proteins was checked using Coomassie staining. Thereafter, the cell liquid having IPTG-induced overexpression was collected and centrifuged to obtain cells. The cells were loosened with 1 ml of DPBS, followed by cell lysis using an ultrasonicator, and then the lysed cells were centrifuged to separate MRS-AIMP3 co-purified protein.

<1-2> Mouse Immunization Through Injection of MRS-AIMP3 Protein

To obtain immunized mice necessary for the preparation of hybridoma cells, the MRS-AIMP3 co-purified protein obtained in Example 1-1 was primarily intraperitoneally injected to four 8- to 10-week old mice. BALB/c mice aged 10 weeks and weighing 25-30 g were purchased from Orient Bio Co. (Sungnam, KyungKiDo, Republic of Korea), and sufficiently acclimated under predetermined conditions for animal breeding (temperature: 20±2° C., humidity: 40-60%, illumination: 12 hours light/dark cycle), and then used in the present study. The animal experiments followed the Institutional Animal Care and Use Committee guidelines of Seoul National University.

Two weeks later, to increase the immunity of the mice after the primary immunization, the same dose of MRS-AIMP3 co-purified protein was secondarily injected into the abdominal cavity of the mice. One week later, the MRS-AIMP3 co-purified protein was booster-injected into the tail vein of the mice three days before cell fusion. After the immunized mice were anesthetized with ether, blood was drawn from the heart using a heparinized syringe, and then the blood was allowed to stand overnight at 4° C. and centrifuged to separate serum. The separated serum was properly divided and stored at −80° C.

<1-3> Preparation of Hybridoma Cells

First, myeloma cells were prepared for cell fusion. The myeloma cells were incubated, and the cell density was set to 2.5 to 5×10$^4$ cell/ml. The myeloma cells were prepared by a 1/3 dilution 24 hours before cell fusion. The mice immunized in Example 1-2 were anesthetized with ether, and then spleens were harvested, followed by B cell isolation. The spleens were washed with SF-DMEM2 (DMEM+2×AA), followed by cell lysis. The cell suspension was collected, placed in a tube, and allowed to stand to settle heavy masses. The supernatant was transferred to a new tube, and then centrifuged at 1500 rpm for 5 minutes. The supernatant of the centrifuged splenocytes was removed, and the tube was tapped and then filled with SF-DMEM2. The B cells and myeloma cells were separately centrifuged and washed, and washing was repeated once more. The supernatant of the washed myeloma cells was removed, and the tube was tapped and then filled with SF-DMEM2. In addition, the supernatant of the washed B cells was removed, and the tube was tapped, and treated by the addition of red blood cells (RBCs) in 1 ml of lysis buffer (LB), and then filled with SF-DMEM2. Then, the B cells and myeloma cells were separately centrifuged, and the supernatants of the centrifuged splenocytes and myeloma cells were removed, and the tube was tapped and then filled with 10 ml of SF-DMEM2. The B cells and myeloma cells were diluted 100-fold in e-tubes, respectively, and counted to determine concentrations thereof [B cell concentrations (1×10$^8$, 8×10$^7$, 5×10$^7$), myeloma cell concentrations (1×10$^7$, 8×10$^6$, 5×10$^6$)]. The B cells and myeloma cells were determined at a ratio of 10:1. The B cells and myeloma cells at the determined concentrations were placed together in a tube and centrifuged. The supernatant of the centrifuged cells was removed, and then the tube was put upside down on an alcohol pad and semi-dried for 30 seconds to 1 minute, and tapped. Pipetting was performed while PEG (2 ml) was slowly added thereto, and the tube was shaken with addition of SF-DMEM2, followed by centrifugation. After the centrifugation, the supernatant was removed and, without tapping, 50 ml of HT medium [HT50×(HT(sigma) 1 vial+SF-DMEM1 10 ml) 1 ml, FBS 10 ml, SF-DMEM1 (DMEM+1×AA) 30 ml] was added dropwise with gradually increasing speed. This suspension was again incubated in a 5% $CO_2$ incubator 37° C. for 3 hours.

<1-4> Screening of Hybridoma Cells Producing MRS-Specific Monoclonal Antibodies

To screen cells specifically recognizing MRS but not AIMP3 in the fusion cell groups prepared in Example 1-3 and investigate the antibody production thereof, the following test was conducted.

First, the medium was exchanged 8-9 days after cell fusion, and incubated in cDMEM2 until the cells were well grown in 96 wells and 24 wells. After medium exchange, the supernatants in wells in which the color has changed were collected and filled with cDMEM2 on day 5-7, and then an ELISA test was performed for the binding of antibodies produced from each fusion cell with MRS and AIMP3. After the ELISA test, wells were selected, and the cells in the selected well were transferred in 24 wells, followed by incubation. After the incubation in 24 wells, an ELISA test was again performed. Specifically, the concentration of fusion cells in 24 wells was checked, and the fusion cells were diluted in 15 ml of the culture solution so as to be 0.5 cell/well in 96-well plates. The fusion cell dilution was dispensed at 150 µl per well. Wells containing one cell were checked by microscopy. The supernatant of the wells containing cells that grew to some extent was collected, and was subjected to primary screening to investigate the binding of the antibodies produced in each fusion cell with MRS and AIMP3. The fusion cells screened on the basis of primary screening were transferred and incubated in 24 wells and centrifuged, and thereafter, the supernatant was collected and subjected to secondary screening through ELISA and Western blotting. The absorbance (OD value) of the fusion cells grown in 24 wells was checked by ELISA to select only fusion cells having an absorbance exceeding 1.0. The selected cells were transferred and incubated in a 25T/C culture flask and centrifuged, and then the supernatant was collected and subjected to tertiary screening through ELISA and Western blotting. The fusion cells screened on the basis of tertiary screening were again transferred and incubated in a 75T/C culture flask, and then the absorbance was checked by ELISA to select cells specifically recognizing MRS but not AIMP3, thereby finally securing "8A12" clones.

<1-5> Culture of Hybridoma Cells Producing MRS-Specific Monoclonal Antibodies and Antibody Production Monoclonal antibodies to MRS can be obtained from the final fusion cells (hybridoma cells "8A12") screened in Example 1-4 through the following two methods. 1) Female mice aged 7-8 weeks were injected with 500 µl of pristane through the abdominal cavity. The fusion cells cultured in the 75T/C culture flask were collected and centrifuged, followed by supernatant removal, and then the cells were placed in a phosphate buffer and pipetted. The fusion cells selected in Example 1-4 were injected in an amount of $8 \times 10^5$ to $4 \times 10^7$ cells into the abdominal cavity of the mice 7-10 days after pristane administration. When the mouse abdominal cavity was full of ascites 12 weeks later, the ascites were extracted using an 18G syringe needle. The ascites were kept at 4° C. overnight, and then centrifuged the next day to remove the mass material containing the yellow layer of fat, and only the supernatant was isolated. The isolated supernatant was dispensed, followed by storage at −20° C.

For the purification of antibodies from the ascites, the column was filled with an appropriate amount of protein A, which was stored in a stock solution (20% ethanol), and 20% ethanol was allowed to flow through the column, and then the column was washed with a 5-bed volume of binding buffer (20 mM sodium phosphate, pH 7.0). The ascites fluid was diluted with an appropriate amount of a phosphate buffer, and was then loaded on the protein A column. After binding with a 3-bed volume of binding buffer (20 mM sodium phosphate, pH 7.0), 10 ml of fractions were each eluted with a 3-bed volume of elution buffer (0.1 M glycine buffer, pH 3.0-2.5). Each fraction was neutralized with 35 µl of a neutralization buffer (1M Tris-HCl, pH 9.0). The fractions were kept in 70% ethanol at a refrigeration temperature overnight, and were then again refrigerated in a stock solution (20% ethanol) until the next use. The fractions were checked for purity through SDS-PAGE, and desalted with Ammersharm GE column.

2) The hybridoma cells obtained in Example 1-4 were cultured at a maximum culture volume of 860 mL using Cellstack-5 (Corning, Corning, N.Y.). GlutaMAX (Gibco) (final 5 mM) and 1× Cholesterol lipid concentrate (Gibco) were added to the serum-less medium (Thermo), and the cells were inoculated at an initial cell concentration of 1.4 to $2.0 \times 10^5$ cell/mL. The cells were removed by centrifugation at 2000 rpm for 10 minutes and the culture supernatant was recovered 4-5 days after inoculation. The pH of the supernatant was checked, and then the pH was adjusted using the prepared 20× binding solution (1M potassium phosphate dibasic, pH 9.0). Thereafter, the supernatant was filtered using a 0.22-um filter to obtain a neutralized antibody culture solution.

The obtained antibody culture solution was purified through a protein A column. After 10 column volumes of distilled water were allowed to flow through the protein A column, an equal amount of a 1× binding solution (50 mM Potassium phosphate dibasic, pH 9.0) was allowed to flow therethrough. Thereafter, the obtained antibody culture solution was allowed to flow therethrough to bind antibodies to protein A, followed by washing with a 1× binding solution (50 mM potassium phosphate dibasic, pH 9.0). To elute the antibodies bound to protein A, 2 column volumes of an elution solution (0.2 M citric acid, pH 3.0) were allowed to flow therethrough, thereby obtaining an eluate. After neutralization with 1 M Tris, the concentration of antibodies was determined by measurement of the absorbance at 280 nm.

Thereafter, the GE PD-10 column was equilibrated with 25 ml of physiological saline and then centrifuged (1000 g, 2 min). Thereafter, 2.5 ml of the antibody eluate obtained from the protein A column was added to the GE PD-10 column, followed by centrifugation (1000 g, 2 min), thereby collecting an antibody solution exchanged with physiological saline. The antibody concentration was determined by measurement of the absorbance at 280 nm, and then the antibody solution was dispensed and stored at −80° C.

<1-6> Antibody Sequencing and Cloning

Cloning and sequencing of 8A12 clone expression antibody was carried out by YBIO Inc. and Abclon Inc. (Korea). Briefly, RNA was first extracted from 8A12 hybridoma cells and cDNA was synthesized. Then, PCR was performed using primers specific to VL, CL, VH, and CH1. PCR products with expected sizes were purified on agarose gel, the sequences thereof were identified through sequencing, and CDR regions were identified through Kabat numbering. The sequencing results of the antigen-binding region are shown in Table 1. Fab was synthesized from the identified sequences, and was confirmed to show high binding ability to MRS through ELISA.

It was also confirmed that the identified sequences match the protein sequencing results (mass spectrometry results) of the antibody obtained through ascites purification after the hybridoma cells in Example 1-5 were injected into the abdominal cavity of the mice.

The obtained 8A12 Fab sequence was cloned into the mouse IgG heavy chain sequence vector (pFUSE-mIgG2a-Fc, InvivoGen) and mouse light chain sequence vector (pFUSE2-CLIg-mK, InvivoGen). Then, the vectors were co-transformed in freestyle 293F cells using PEI (Polysciences, 23966-2), so that antibody heavy and light chains were co-expressed together in the cells. The transformed 293F cells were incubated under conditions of 37° C. and 8% $CO_2$ for 7 days. Then, the cells were obtained and centrifuged, thereby obtaining the supernatant. The pH of the supernatant was checked, and then the pH of the supernatant was adjusted to 7.6 using the prepared 20× binding solution (1M potassium phosphate dibasic, pH 9.0). Thereafter, the supernatant was filtered using a 0.22-um filter to obtain a neutralized antibody culture solution. An antibody was obtained from the antibody culture solution by the method described in 2) of Example 1-5. It was confirmed that the whole 8A12 IgG antibody thus obtained is composed of a light chain containing the amino acid sequence of SEQ ID NO: 18 and a heavy chain containing the amino acid sequence of SEQ ID NO: 19.

TABLE 1

| | | Amino acid sequence | DNA sequence |
|---|---|---|---|
| VH | FR1 | DVKLQESGPGL VKPSQSLSLTC TVTGYSIT | gatgtgaagcttcaggagtcgggac ctggcctggtgaaacctttctcagtc tctgtccctcacctgcactgtcact ggctattcaatcacc |
| | CDR-H1 | SEYAWT | agtgagtatgcctggacc |
| | FR2 | WIRQFPGNKLE WMG | tggatccggcagtttccaggaaaca aactggaatggatgggc |

TABLE 1-continued

| | | Amino acid sequence | DNA sequence |
|---|---|---|---|
| | CDR-H2 | YINYNGNTNLN PSLKS | tacataaactacaatggcaacacta acttaaatccatctctcaaaagt |
| | FR3 | RISIIRDTSKN QFFLQLNSVTT EDTATYYCAR | cgaatctctatcattcgagacacat ccaagaaccagttcttcctgcagtt gaattctgtgacaactgaggacaca gccacatattactgtgcaaga |
| | CDR-H3 | SLWPRGWFAY | tcactttggcccaggggctggtttg cttac |
| | FR4 | WGQGTLVTVSA | tggggccaagggactctggtcactg tctctgca |
| VL | FR1 | DIQMTQSPSSM YASLGERVTIT C | gacattCtgatgacccagtctccat cttccatgtatgcatctctaggaga gagagtcactatcacttgc |
| | CDR-L1 | KASQDINSYLS | aaggcgagtcaggacattaatagct atttaagc |
| | FR2 | WFQQKPGKSPK TLMY | tggttccagcagaaaccagggaaat ctcctaagaccctgatgtat |
| | CDR-L2 | RANRLVD | cgtgcaaacagattggtagat |
| | FR3 | GVPSRFSGSGS GQDYSLTISSL EYEDMGIYYC | ggggtcccatcaaggttcagtggca gtggatctggccaagattattctct caccatcagcagcctggaatatgaa gatatgggaatttattattgt |
| | CDR-L3 | LQYDEFPRT | ctacagtatgatgagtttcctcgga cg |
| | FR4 | FGGGTKLEIK | ttcggtggaggcaccaagctggaaa tcaaa |

<1-7> Comparison of Binding Specificity of Antibody to MRS—Western Blotting

To investigate the MRS binding ability of the 8A12 antibody obtained in the above example, the following test was performed. H460 cells were incubated in DMEM (Hy-Clone, GE Life Sciences) containing 10% fetal bovine serum (FBS, HyClone, GE Life Sciences) and 1% penicillin (HyClone, GE Life Sciences). All the cells were incubated under conditions of 5% $CO_2$ and 37° C. The incubated H460 cells were treated with si-MRS for 72 hours. Then, the H460 cells were obtained and lysed, and then the H460 cell lysate was subjected to Western blotting. The test was repeated twice. The 8A12 antibody as a primary antibody was diluted to 1:5000 (0.2 µg/ml) before use and, for comparison of binding ability, currently commercially available MRS antibody (Abcam, Ab50793) was used by the same method, and tubulin was used as a control.

Figure 1:
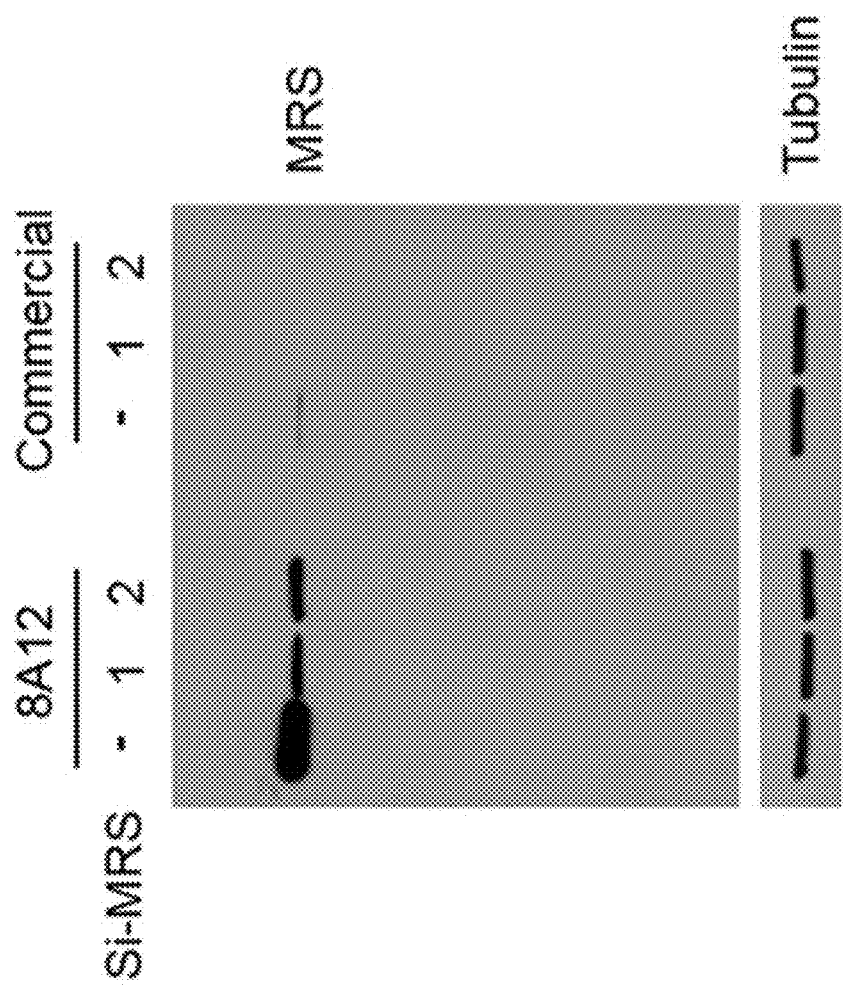
FIG. 1 shows Western blotting results comparing MRS binding strength of 8A12 antibody with that of a known commercial MRS antibody, wherein cell eluates of H460 cells, treated with si-MRS, were used.

As a test result, as shown in FIG. 1, the currently commercially available MRS antibody never detected MRS in the si-MRS treatment group and showed significantly low detection ability (binding ability with MRS) compared with the 8A12 antibody of the present invention even in the si-MRS non-treatment group. Whereas, the 8A12 antibody of the present invention was confirmed to have excellent MRS-specific binding ability compared with the conventional commercial MRS antibody.

<1-8> Verification on Cross-Activity with Other Proteins—ELISA

To investigate whether the 8A12 antibody acquired in the above example had cross-activity with other aminoacyl-tRNA synthetase (ARS) proteins, the following test was performed.

On a 96-well plate (Corning 3690 flat bottom, 96-well half-area plates), MRS proteins (His-MRS, MRS full) and other ARS proteins (DX2 tag free, 34S-DX2, 34S-AIMP2, His-CRS, His-AIMP1, His-GRS, His-WRS, His-KRS) were each coated at a concentration of 1 µg/ml. 8A12 antibody was added at a concentration of 500 ng/ml to the 96-well plate coated with coated with each of the ARS proteins, followed by incubation for 1 hour. Thereafter, HRP-conjugated anti-mouse IgG secondary antibody was added, followed by incubation for 1 hour, and the absorbance at 450 nm was measured by ELISA. As a substrate, 3,3',5,5'-tetramethylbenzidine (TMB) was used.

Figure 2:
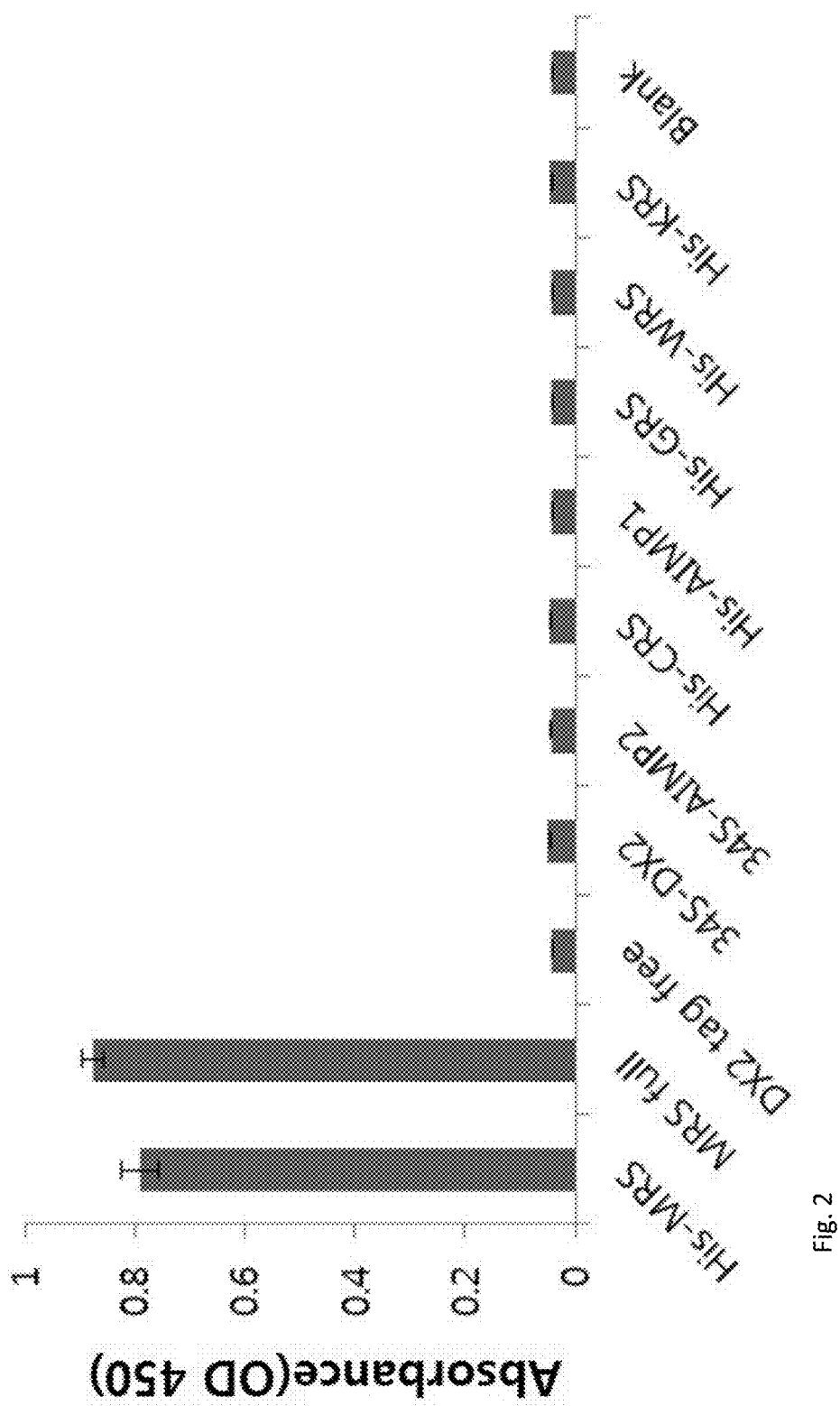
FIG. 2 shows a graph depicting ELISA results to investigate the cross-activity of 8A12 antibody with other aminoacyl-tRNA synthetase (ARS) and AIMP proteins.

As a result, as shown in FIG. 2, the 8A12 antibody bound to and reacted with only MRS, but not with other ARS and AIMP proteins. The results confirmed that the 8A12 antibody had no cross-activity with other ARS and AIMP proteins and specifically detected only MRS.

<1-9> Verification of Antibody Affinity Using Surface Plasmon Resonance

To investigate MRS-specific affinity of the 8A12 antibody, a surface plasmon resonance (SPR) test was performed using MRS-AIMP3 co-purified protein (hereinafter, MRS+AIMP3 protein) and AIMP3 protein. MRS+AIMP3 or AIMP3 protein was coated on a CM5 chip and the 8A12 antibody was allowed to flow down, thereby measuring the degree of binding response of the protein. An analyte sample or buffer was injected at a flow rate of 30 µl/min for 8 minutes, and washed for 20 minutes.

Figure 3:
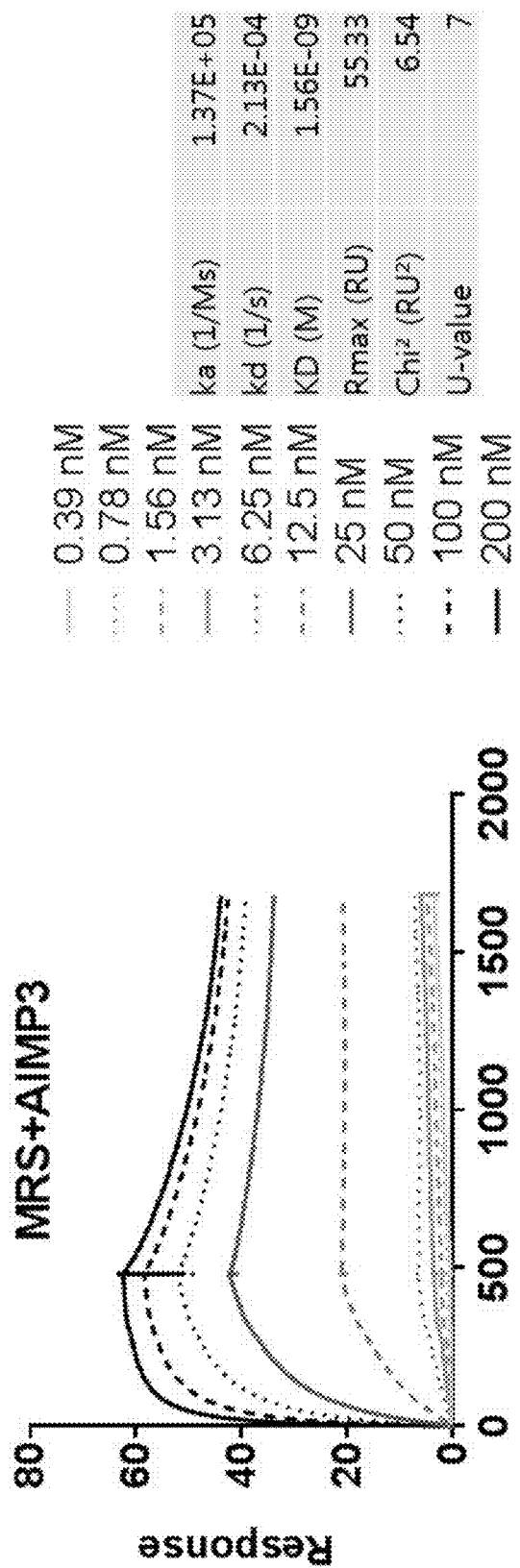
FIG. 3 shows surface plasmon resonance (SPR) test results to investigate antibody affinity of 8A12 antibody to MRS+AIMP3 protein.
Figure 4:
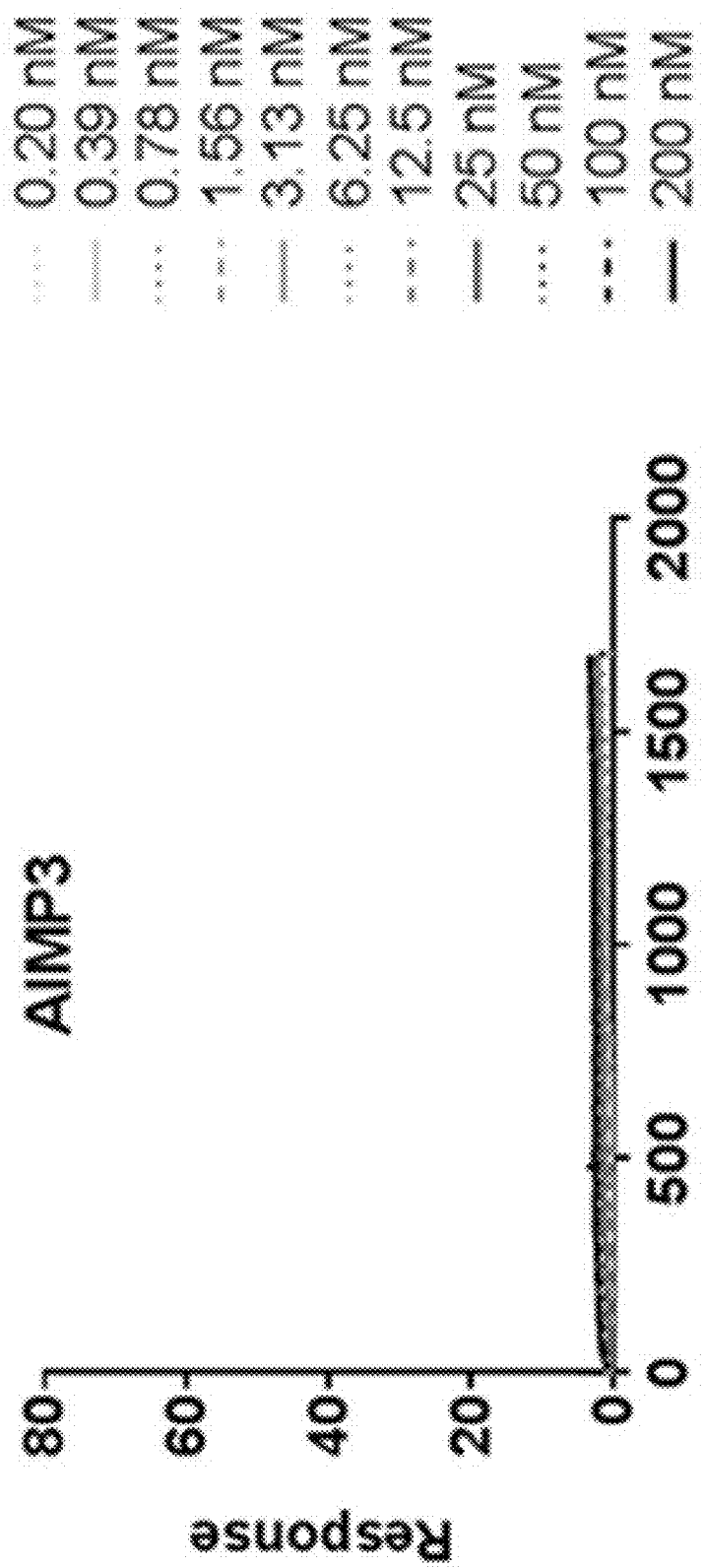
FIG. 4 shows surface plasmon resonance (SPR) test results confirming that 8A12 antibody had no response to AIMP3.

As shown in FIGS. 3 and 4, the results confirmed that the 8A12 antibody bound to the MRS+AIMP3 protein but not the AIMP3 protein. It could also be confirmed that the 8A12 antibody has a KD value of 1.56 nM to MRS.

<1-10> Verification of Binding Site of MRS Antibody

To investigate the binding site (epitope) for the 8A12 antibody, the following test was performed.

First, several MRS fragments with different lengths and loci were constructed in consideration of GST, catalytic domain, and tRNA binding domain sites in the MRS whole protein, and the MRS whole protein or each MRS fragment was cloned into the pcDNA3 vector (EV). The loci of the respective MRS fragments were selected at loci comprising several small unit domains, including the fragment of aa 1-266, fragment of aa 267-597, fragment of aa 1-598, fragment of aa 598-900, fragment of aa 660-860, fragment of aa 660-900, fragment of aa 730-900, and the like. Here, the Myc protein was bound to the N-terminal of each peptide, and the Myc protein was used as a control. Then, 2 µg of vector DNA cloned in H460 cells was transfected using Turbofect (Thermo) according to the instruction of the manufacturer. After 24 hours, the cells were obtained and Western blotting was performed. Here, the 8A12 was diluted at 1:5000 (0.2 µg/mL) before use.

Through the test, the epitope for the 8A12 antibody was confirmed to be present in at least a region of aa 861-900 in the MRS protein of SEQ ID NO: 1.

Therefore, various small-unit fragment peptides, including the fragment of aa 811-840, the fragment of aa 821-850, the fragment of aa 831-860, the fragment of aa 841-870, the fragment of aa 846-875, the fragment of aa 851-880, the fragment of aa 856-885, the fragment of aa 861-890, the fragment of aa 866-895, the fragment of aa 871-900, were constructed, and each peptide was coated at 300 ng/well in the 96-well ELISA plate, and was subjected to ELISA according to the protocol. The 8A12 antibody as a primary antibody was diluted to 10 nM (1×PBST-Tween 0.05%), and HRP-conjugated Goat anti-mouse IgG (Thermo) as a secondary antibody was diluted at 1:10000 (1×PBST-Tween 0.05%), and the absorbance was measured at 450 nm.

The test results confirmed that the 8A12 antibody specifically recognized, as an epitope, the region of aa 851-880 (KQGNIVRELKAQKADKNEVAAEVAKLLDLK, SEQ ID NO: 20) in the MRS protein. These test results indicate that other binding molecules (other antibodies and functional fragments thereof) recognizing the region of aa 851-880 as an epitope would also have excellent MRS-specific binding ability and MRS discrimination ability.

Hereinafter, an example employing the antibody with excellent MRS detection ability constructed above will be shown for novel bile duct cancer examination methods designed by the present inventors.

Example 2

Establishment of Bile Duct Cancer-Cell-Specific MRS Expression Detecting Method (Staining Method) and Confirmation of Effect Thereof, in Cytodiagnosis 1) A specimen was obtained according to brush cytology (Osnes M, Serck-Hanssen A, Myren J. Scand J Gastroenterol. 1975; 10(8):829-31). Specifically, bile duct brushing was performed using a GRBH-230-3-3.5 brush (Wilson-Cook Medical, Inc., Winston-Salem, N.C.). A brush was allowed to make five to eight times of to-and-fro movement across the lesion site. Thereafter, the brush was washed with Roswel Park Memorial Institute (RPMI) 1640 medium (GibcoBRL, Rockville, Mass., USA), and then immediately moved to the cytology laboratory for liquid-based cytology examination (Thinprep). The brush was shaken in the Thin-Prep fixative liquid (PreservvCyt solution) to liberate bile duct cells. The specimen (bile duct cells) thus obtained was smeared on the ThinPrep slide by an ordinary method using ThinPrep (Hologic Inc) to prepare cell samples. The cell samples were each subjected to the following examination method, and the results thereof were compared.

2) Pathological findings by a conventional cytology were made by Pap staining, which has been frequently used to date, and the Pap staining was performed using hematoxylin, Orange G-6 (OG-6), or eosin azure according to the ordinary protocol. The Pap-stained specimens were morphologically analyzed. The cells were determined to be benign (normal) cells when: the cells were smeared in one layer on the ThinPrep slide; the nucleus/cytoplasm ratio (N/C ratio) is small; and the nuclear membrane has a smooth shape. The cells were determined to be malignant cells when: cells were three-dimensionally smeared; the nucleus/cytoplasm ratio was high; chromatin agglomeration appeared; and the nuclear membrane had a rough shape; and nucleoli and mitosis appeared. The cells were determined to be atypical cells when the cell change did not reach malignant cells but could not be diagnosed with benign.

3) The final clinical diagnosis was made by doctors through a comprehensive final determination on the basis of the measurement results by imaging examinations (abdominal ultrasound, abdominal computed tomography, abdominal magnetic resonance imaging, endoscopic retrograde cholangiogram, and positron emission tomography) and pathological examinations (cytodiagnosis and biopsy).

4) The present inventors developed immunofluorescence staining for measuring the degree of expression of MRS in bile duct cells and normal bile duct cells (including benign bile duct stricture cells but not cancer cells) as follows. Specifically, the ThinPrep slide samples were treated as follows.

① D.W washing, twice

② Pre-treatment: Incubate with PBS containing 2% normal goat serum, 0.1% Tween-20, and 0.09% sodium azide at room temperature for 1 hour (incubation)

③ Primary antibody treatment: Incubate with MRS antibody, diluted to 2 μg/ml in PBS (containing 0.1% BSA and 0.09% sodium azide), at room temperature for 1 hour MRS antibody (8A12 antibody) having light chain containing the amino acid sequence of SEQ ID NO: 18 and heavy chain containing the amino acid sequence of SEQ ID NO: 19 being used in the present test ④ Wash twice with 1× washing solution TBST (1×TBS with 0.01% Tween-20)

⑤ Color development: Incubate with secondary antibody (Goat-anti-mouse IgG(H+L)-Alexa Fluor 488 (Thermo, cat #A11001)), diluted at 1:100 in PBS (containing 0.1% BSA, 0.09% sodium azide), at room temperature for 1 hour ⑥ Wash twice with 1× washing solution TBST (1×TBS with 0.01% Tween-20)

⑦ Apply DAPI (Invitrogen P36931), and then cover with cover glass

Out of the samples, the cells showing a degree of MRS staining that was more than doubled compared with the negative control were determined to be bile duct cancer cells, and these results were compared with pathological findings and final diagnosis results for the specimens to investigate the accuracy of diagnosis (sensitivity and specificity). The results are shown in Tables 2 and 4 below.

TABLE 2

Comparative details: Comparison of examination results between conventional cytology and MRS immunostaining of present invention, on the basis of final clinical pathological diagnosis results

| Conventional cytology | Final clinical pathological diagnosis | MRS immunostaining | |
|---|---|---|---|
| | | Positive | Negative |
| positive for Malignancy (n = 18) | Malignancy(n = 18) | 18 | 0 |
| | Benign(n = 0) | 0 | 0 |
| Suspicious of malignancy (n = 16) | Malignancy(n = 15) | 14 | 1 |
| | Benign(n = 1) | 1 | 0 |
| Atypia(n = 26) | Malignancy(n = 15) | 15 | 0 |
| | Benign(n = 11) | 0 | 11 |
| Negative for malignancy (n = 13) | Malignancy(n = 0) | 0 | 0 |
| | Benign(n = 13) | 0 | 13 |

TABLE 3

Comparative summarization: Comparison of examination results between conventional cytology and MRS immunostaining of present invention, on the basis of final clinical pathological diagnosis results (determinations of positive for malignancy and suspicious malignancy in conventional cytology results on Table 2 above being classified as final positive, and determination of atypia and negative for malignancy being classified as final negative)

| | | Final clinical pathological diagnosis results | |
|---|---|---|---|
| | | Malignancy (n = 48) | Benign (n = 25) |
| Convenetional cytology | Positive (n = 34) | 33 | 1 |
| | Negative (n = 39) | 15 | 24 |
| MRS immunostaining | Positive (n = 48) | 47 | 1 |
| | Negative (n = 25) | 1 | 24 |

TABLE 4

Comparison of sensitivity, specificity, positive predictive value (PPV), negative predictive value, and accuracy of diagnosis between conventional cytology and MRS immunostaining of present invention

|  | Sensitivity (%) | Specificity (%) | Accuracy (%) | PPV (%) | NPV (%) |
|---|---|---|---|---|---|
| Conventional cytology | 68.8 | 96 | 78.1 | 97.1 | 61.5 |
| MRS immunostaining | 97.9 | 96 | 97.2 | 97.9 | 96 |

As a test result, as shown in Tables 2 to 4, the MRS immunostaining examination provided in the present invention showed a sensitivity of 97.9% and a specificity of 96%, almost 100%, and an accuracy of 97.2%, compared with the conventional cytological examination. These results indicate that the examination method of the present invention can accurately detect and discriminate bile duct cells and normal bile duct cells (including benign bile duct stricture cells but not cancer) at almost 100% in the diagnosis at the cellular level, which are significantly compared with the level of accuracy, 78.1%, of the conventionally used cytological examination.

Figure 5:
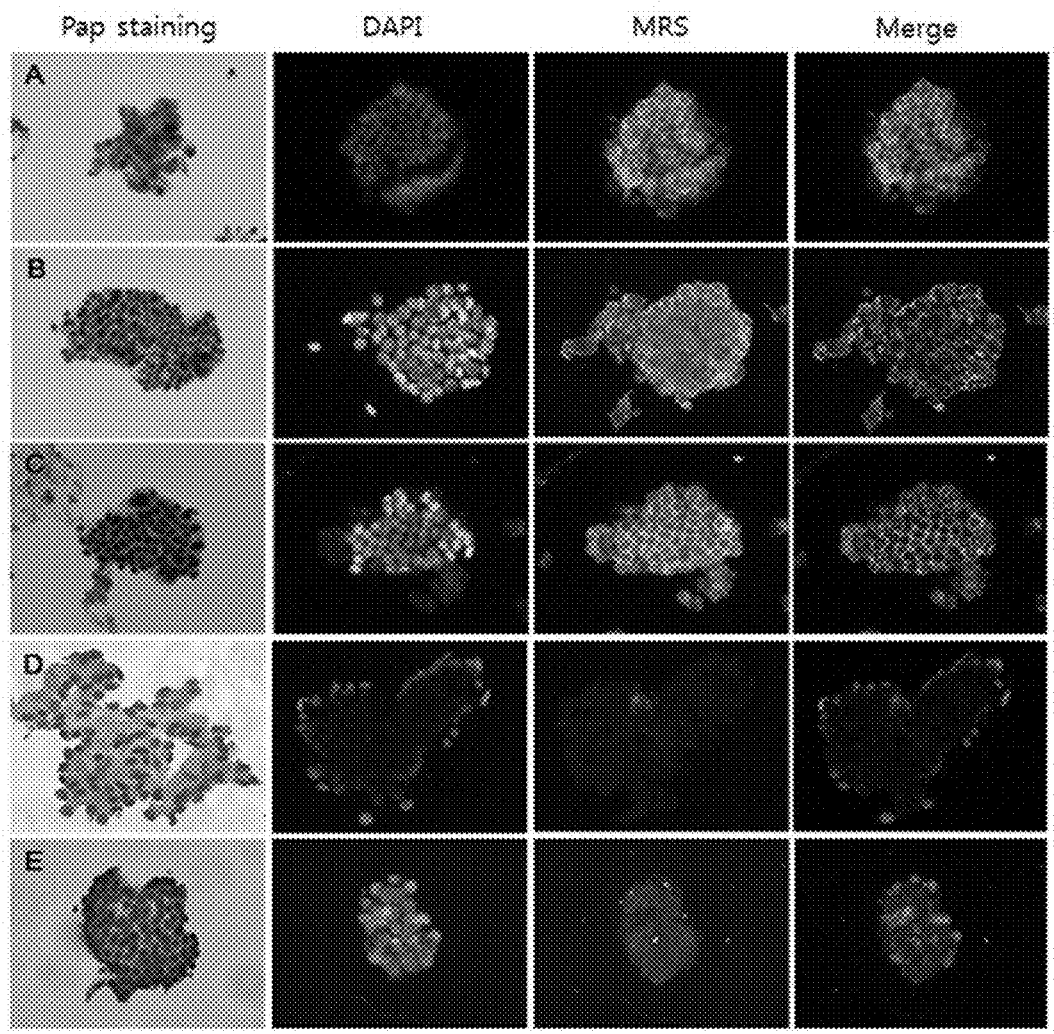
FIG. 5 comparatively shows morphological observation results after Pap staining as a conventional cytology and application results of MRS immunostaining examination of the present invention in several diagnostic examples for bile duct cancer, wherein ×400 magnification microscope images are shown (all of the following test groups was subjected to the MRS staining method of the present invention while the diagnosis for corresponding samples was unknown).

FIG. 5 shows representative diagnosis examples for the respective diagnosis types on Table 2. In the bile duct cancer cells, MRS was widely distributed in the cell membrane and cytoplasm and strong staining signals were observed (see from A to C of FIG. 5), and in the normal (benign) cells, negative or very weak staining signals were observed in the region including the cytoplasm (see D and E of FIG. 5). The above test confirmed that the novel MRS staining method provided in the present invention is a very useful staining method with high sensitivity and specificity in bile duct cancer cell cytodiagnosis. Especially, even atypical cells, which are difficult to differentiate using a conventional staining method on a specimen obtained by brush cytology, can be differentiated according to the staining or non-staining of MRS, and it is therefore thought that the cyto-diagnosis method according to the present invention alone can be used to make an accurate clinical diagnosis of bile duct cancer.

Example 3

Establishment of Bile Duct Cancer-Cell-Specific MRS Expression Detecting Method and Confirmation of Effect Thereof in Biopsy Immunohistochemistry (IHC) for measuring the degree of expression of MRS in bile duct cancer tissue and normal bile duct tissue (including benign bile duct stricture cells but not cancer) was developed as follows. Specifically, 55 unknown bile duct biopsy tissue samples were generally paraffin-embodied and sectioned. Thereafter, a final specimen was obtained by the treatment in the following order:

① Soak sectioned tissue in xylene for 24 hours→treat with 100% alcohol for 2 minutes twice→treat with 100% alcohol for 2 minutes once→treat with 90% alcohol for 2 minutes twice→treat with 70% alcohol for 2 minutes once→DW washing twice or three times ② Antigen retrieval: Dilute commercial citrate buffer (DW 9: citrate buffer 1), preheat for 2 minutes, put slide therein, and then heat for 10 minutes (microwave oven)

③ Heat, and then immediately soak in tap water twice to cool—wash with 1TBST for 5 minutes three times ④ Treat with 0.3% $H_2O_2$ at room temperature for 1 hour→block (2% goat serum+2% BSA, 1PBS base) at room temperature for 30 minutes ⑤ Primary antibody (MRS antibody) 1:Dilute at 1:500, and then incubate at room temperature overnight→Wash with 1TBST for 5 minutes three times MRS antibody having light chain containing the amino acid sequence of SEQ ID NO: 8 and heavy chain containing the amino acid sequence of SEQ ID NO: 19 being used in the present test ⑥ Apply HRP (secondary antibody) and then incubate at room temperature for 30 minutes→Wash with 1TBST for 5 minutes three times ⑦ Apply DAB for 1 minute, followed by color development, and wash with DW twice or three times→apply hematoxylin for 3 minutes, followed by color development, and then wash with DW twice or three times ⑧ Treat with 70% alcohol for 2 minutes once→treat with 90% alcohol for 2 minutes once→treat with 95% alcohol for 2 minutes once→treat with 100% alcohol for 2 minutes twice→treat with xylene for 5 minutes three times ⑨ Apply mounting solution and then cover with cover glass In the sample, when MRS was strongly stained in the infiltrating cells compared with pancreatic acinar cells as an internal control, such cells were determined to be bile duct cancer cells, and these results were compared with the final clinical diagnosis results for the specimen to investigate the accuracy of diagnosis (sensitivity and specificity), and the results are shown in Table 5. The final clinical diagnosis results were comprehensively and finally made by doctors.

TABLE 5

Results of MRS immunostaining examination of present invention on bile duct cancer tissue and normal bile duct tissue

| Final clinical pathological diagnosis | Number of specimens | MRS immunostaining of present invention | | Positive rate† |
|---|---|---|---|---|
| | | Positive | Negative | |
| Bile duct cancer tissue | 45 | 45 | 0 | 100 |
| Normal bile duct tissue | 10 | 0 | 10 | 0 |

†Positive rate being expressed as % of degree of MRS exprssion

As shown in Table 5, the test results confirmed that the bile duct cancer tissue and the normal bile duct tissue can be discriminatively detected with 100% sensitivity and specificity through the detection method (staining method) provided in the present invention. FIGS. 6 to 8 show representative diagnosis examples for respective types in the diagnosis of 55 specimens on Table 5. Especially, the results were shown to match the pathological findings through H&E staining (the morphological diagnosis method through H&E being similar to that in the foregoing Example 2), which is a conventional bile duct-tissue-staining method.

As set forth above, the present invention relates to a method for diagnosing bile duct cancer in bile duct cells by using methionyl-tRNA synthetase (MRS). More specifically, the present invention relates to a composition for diagnosing bile duct cancer, the composition comprising an agent for measuring the expression level of a methionyl-tRNA synthetase protein, a diagnostic kit, and a method for qualitatively or quantitatively analyzing MRS to provide information necessary for the diagnosis of bile duct cancer.

MRS is overexpressed only for bile duct cancer, as differentiating between normal cells and other benign bile duct diseases, and the use of MRS can attain a definite diagnosis of bile duct cancer with almost 100% sensitivity, specificity, and accuracy for even indeterminate atypical cells determined through conventional cytodiagnosis pathological examinations. Therefore, MRS is valuable as a diagnostic maker for bile duct cancer, and thus is highly applicable in the field of in-vitro diagnostic industry.

The invention claimed is:

1. A method for treating a bile duct cancer in a latent patient, the method comprising the steps of:
   obtaining a sample from a latent patient;
   measuring the expression level of a methionyl-tRNA synthetase (MRS) protein in the sample;
   comparing the measured protein expression level of the latent patient with that of a control;
   diagnosing the patient with a bile duct cancer when the protein expression level of the patient is increased in comparison with that of the control; and
   treating the diagnosed patient by conducting at least one of a chemotherapy, a surgery, and a radiation therapy.

2. The method of claim 1, wherein the methionyl-tRNA synthetase protein contains the amino acid sequence defined by SEQ ID NO: 1.

3. The method of claim 1, wherein the step of measuring is conducted by an agent which comprises an antibody specifically binding to the methionyl-tRNA synthetase (MRS) protein.

4. The method of claim 1, wherein the step of diagnosing is conducted by a kit which comprises an agent for measuring the expression level of a methionyl-tRNA synthetase (MRS) protein, wherein the agent comprises an antibody specifically binding to the methionyl-tRNA synthetase (MRS) protein.

5. The method of claim 1, wherein the sample is bile duct cells.

6. The method of claim 5, wherein the method further comprises the following steps before, simultaneously with, or after the step of measuring:
   (i) staining the bile duct cells with: at least one nucleus-staining solution selected from the group consisting of 4',6-diamidino-2-phenylindole (DAPI), methylene blue, acetocarmine, toluidine blue, hematoxylin, and Hoechst, and at least one cytoplasm-staining solution selected from the group consisting of eosin, crystal violet, and Orange G; and
   (ii) determining by said cell staining that the bile duct cells are malignant tumor cells, atypical cells, or normal cells.

7. The method of claim 5, wherein the bile duct cells are collected by brush cytology.

8. The method of claim 1, wherein the expression level of the protein is measured using any one of Western blotting, ELISA, radioimmunoassay, radioimmunodiffusion, Ouchterlony immunodiffusion, rocket immunoelectrophoresis, immunostaining, immunoprecipitation assay, complement fixation assay, FACS, or protein chip assay.

9. The method of claim 3, wherein the antibody is an antibody or a functional fragment thereof, which specifically binds to an epitope region of MRS containing the amino acid sequence defined by SEQ ID NO: 20, wherein the antibody comprises:
a light chain variable region (VL) containing the amino acid sequence defined by SEQ ID NO: 14; and
a heavy chain variable region (VH) containing the amino acid sequence defined by SEQ ID NO: 16.

10. The method of claim 6, wherein in step (ii), it is determined by cell-staining results of step (i) that:
the bile duct cells are malignant cells when there are two or more types of morphological abnormality selected from the group consisting of: three-dimensional smear of cells, a high nucleus/cytoplasm ratio (N/C ratio), an appearance of chromatin agglomeration; a rough-shaped nuclear membrane, an appearance of nucleoli, and an appearance of mitosis;
the bile duct cells are normal cells when the cells are smeared in one layer, the nucleus/cytoplasm ratio (N/C ratio) is low, and the nuclear membrane has a smooth shape; and
the bile duct cells are atypical cells when the extent of a cell change does not reach that of malignant cells but cannot be diagnosed as normal.

11. The method of claim 6, wherein the bile duct cells are collected by brush cytology.

\* \* \* \* \*

```
                         SEQUENCE LISTING

<160> NUMBER OF SEQ ID NOS: 21

<210> SEQ ID NO 1
<211> LENGTH: 900
<212> TYPE: PRT
<213> ORGANISM: Artificial Sequence
<220> FEATURE:
<223> OTHER INFORMATION: Description of Artificial Sequence: Synthetic
      amino acid sequence of methionyl-tRNA synthetase

<400> SEQUENCE: 1

Met Arg Leu Phe Val Ser Asp Gly Val Pro Gly Cys Leu Pro Val Leu
1               5                   10                  15

Ala Ala Ala Gly Arg Ala Arg Gly Arg Ala Glu Val Leu Ile Ser Thr
            20                  25                  30

Val Gly Pro Glu Asp Cys Val Val Pro Phe Leu Thr Arg Pro Lys Val
        35                  40                  45

Pro Val Leu Gln Leu Asp Ser Gly Asn Tyr Leu Phe Ser Thr Ser Ala
    50                  55                  60

Ile Cys Arg Tyr Phe Phe Leu Leu Ser Gly Trp Glu Gln Asp Asp Leu
65                  70                  75                  80

Thr Asn Gln Trp Leu Glu Trp Glu Ala Thr Glu Leu Gln Pro Ala Leu
                85                  90                  95

Ser Ala Ala Leu Tyr Tyr Leu Val Val Gln Gly Lys Lys Gly Glu Asp
            100                 105                 110

Val Leu Gly Ser Val Arg Arg Ala Leu Thr His Ile Asp His Ser Leu
        115                 120                 125

Ser Arg Gln Asn Cys Pro Phe Leu Ala Gly Glu Thr Glu Ser Leu Ala
    130                 135                 140

Asp Ile Val Leu Trp Gly Ala Leu Tyr Pro Leu Leu Gln Asp Pro Ala
145                 150                 155                 160

Tyr Leu Pro Glu Glu Leu Ser Ala Leu His Ser Trp Phe Gln Thr Leu
                165                 170                 175

Ser Thr Gln Glu Pro Cys Gln Arg Ala Ala Glu Thr Val Leu Lys Gln
            180                 185                 190

Gln Gly Val Leu Ala Leu Arg Pro Tyr Leu Gln Lys Gln Pro Gln Pro
        195                 200                 205

Ser Pro Ala Glu Gly Arg Ala Val Thr Asn Glu Pro Glu Glu Glu Glu
    210                 215                 220

Leu Ala Thr Leu Ser Glu Glu Glu Ile Ala Met Ala Val Thr Ala Trp
225                 230                 235                 240

Glu Lys Gly Leu Glu Ser Leu Pro Pro Leu Arg Pro Gln Gln Asn Pro
                245                 250                 255

Val Leu Pro Val Ala Gly Glu Arg Asn Val Leu Ile Thr Ser Ala Leu
            260                 265                 270

Pro Tyr Val Asn Asn Val Pro His Leu Gly Asn Ile Ile Gly Cys Val
        275                 280                 285

Leu Ser Ala Asp Val Phe Ala Arg Tyr Ser Arg Leu Arg Gln Trp Asn
    290                 295                 300

Thr Leu Tyr Leu Cys Gly Thr Asp Glu Tyr Gly Thr Ala Thr Glu Thr
305                 310                 315                 320
```

```
Lys Ala Leu Glu Glu Gly Leu Thr Pro Gln Glu Ile Cys Asp Lys Tyr
            325                 330                 335

His Ile Ile His Ala Asp Ile Tyr Arg Trp Phe Asn Ile Ser Phe Asp
            340                 345                 350

Ile Phe Gly Arg Thr Thr Thr Pro Gln Gln Thr Lys Ile Thr Gln Asp
            355                 360                 365

Ile Phe Gln Gln Leu Leu Lys Arg Gly Phe Val Leu Gln Asp Thr Val
    370                 375                 380

Glu Gln Leu Arg Cys Glu His Cys Ala Arg Phe Leu Ala Asp Arg Phe
385                 390                 395                 400

Val Glu Gly Val Cys Pro Phe Cys Gly Tyr Glu Glu Ala Arg Gly Asp
                405                 410                 415

Gln Cys Asp Lys Cys Gly Lys Leu Ile Asn Ala Val Glu Leu Lys Lys
                420                 425                 430

Pro Gln Cys Lys Val Cys Arg Ser Cys Pro Val Val Gln Ser Ser Gln
                435                 440                 445

His Leu Phe Leu Asp Leu Pro Lys Leu Glu Lys Arg Leu Glu Glu Trp
    450                 455                 460

Leu Gly Arg Thr Leu Pro Gly Ser Asp Trp Thr Pro Asn Ala Gln Phe
465                 470                 475                 480

Ile Thr Arg Ser Trp Leu Arg Asp Gly Leu Lys Pro Arg Cys Ile Thr
                485                 490                 495

Arg Asp Leu Lys Trp Gly Thr Pro Val Pro Leu Glu Gly Phe Glu Asp
                500                 505                 510

Lys Val Phe Tyr Val Trp Phe Asp Ala Thr Ile Gly Tyr Leu Ser Ile
    515                 520                 525

Thr Ala Asn Tyr Thr Asp Gln Trp Glu Arg Trp Trp Lys Asn Pro Glu
    530                 535                 540

Gln Val Asp Leu Tyr Gln Phe Met Ala Lys Asp Asn Val Pro Phe His
545                 550                 555                 560

Ser Leu Val Phe Pro Cys Ser Ala Leu Gly Ala Glu Asp Asn Tyr Thr
                565                 570                 575

Leu Val Ser His Leu Ile Ala Thr Glu Tyr Leu Asn Tyr Glu Asp Gly
                580                 585                 590

Lys Phe Ser Lys Ser Arg Gly Val Gly Val Phe Gly Asp Met Ala Gln
            595                 600                 605

Asp Thr Gly Ile Pro Ala Asp Ile Trp Arg Phe Tyr Leu Leu Tyr Ile
            610                 615                 620

Arg Pro Glu Gly Gln Asp Ser Ala Phe Ser Trp Thr Asp Leu Leu Leu
625                 630                 635                 640

Lys Asn Asn Ser Glu Leu Leu Asn Asn Leu Gly Asn Phe Ile Asn Arg
                645                 650                 655

Ala Gly Met Phe Val Ser Lys Phe Phe Gly Gly Tyr Val Pro Glu Met
                660                 665                 670

Val Leu Thr Pro Asp Asp Gln Arg Leu Leu Ala His Val Thr Leu Glu
                675                 680                 685

Leu Gln His Tyr His Gln Leu Leu Glu Lys Val Arg Ile Arg Asp Ala
            690                 695                 700

Leu Arg Ser Ile Leu Thr Ile Ser Arg His Gly Asn Gln Tyr Ile Gln
705                 710                 715                 720

Val Asn Glu Pro Trp Lys Arg Ile Lys Gly Ser Glu Ala Asp Arg Gln
                725                 730                 735
```

```
Arg Ala Gly Thr Val Thr Gly Leu Ala Val Asn Ile Ala Ala Leu Leu
            740                 745                 750

Ser Val Met Leu Gln Pro Tyr Met Pro Thr Val Ser Thr Ile Gln
        755                 760                 765

Ala Gln Leu Gln Leu Pro Pro Pro Ala Cys Ser Ile Leu Leu Thr Asn
    770                 775                 780

Phe Leu Cys Thr Leu Pro Ala Gly His Gln Ile Gly Thr Val Ser Pro
785                 790                 795                 800

Leu Phe Gln Lys Leu Glu Asn Asp Gln Ile Glu Ser Leu Arg Gln Arg
                805                 810                 815

Phe Gly Gly Gly Gln Ala Lys Thr Ser Pro Lys Pro Ala Val Val Glu
            820                 825                 830

Thr Val Thr Thr Ala Lys Pro Gln Gln Ile Gln Ala Leu Met Asp Glu
        835                 840                 845

Val Thr Lys Gln Gly Asn Ile Val Arg Glu Leu Lys Ala Gln Lys Ala
    850                 855                 860

Asp Lys Asn Glu Val Ala Ala Glu Val Ala Lys Leu Leu Asp Leu Lys
865                 870                 875                 880

Lys Gln Leu Ala Val Ala Glu Gly Lys Pro Pro Glu Ala Pro Lys Gly
                885                 890                 895

Lys Lys Lys Lys
        900

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      amino acid sequence of 8A12 VL CDR1

<400> SEQUENCE: 2

Lys Ala Ser Gln Asp Ile Asn Ser Tyr Leu Ser
1               5                   10

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      nucleotide sequence of 8A12 VL CDR1

<400> SEQUENCE: 3
aaggcgagtc aggacattaa tagctattta agc                              33

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence of 8A12 VL CDR2

<400> SEQUENCE: 4

Arg Ala Asn Arg Leu Val Asp
1               5

<210> SEQ ID NO 5
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      nucleotide sequence of 8A12 VL CDR2

<400> SEQUENCE: 5
cgtgcaaaca gattggtaga t                                              21

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence of 8A12 VL CDR3

<400> SEQUENCE: 6

Leu Gln Tyr Asp Glu Phe Pro Arg Thr
1               5

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      nucleotide sequence of 8A12 VL CDR3

<400> SEQUENCE: 7
ctacagtatg atgagtttcc tcggacg                                        27

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      amino acid sequence of 8A12 VH CDR1

<400> SEQUENCE: 8

Ser Glu Tyr Ala Trp Thr
1               5

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      nucleotide sequence of 8A12 VH CDR1

<400> SEQUENCE: 9
agtgagtatg cctggacc                                                  18

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      amino acid sequence of 8A12 VH CDR2

<400> SEQUENCE: 10

Tyr Ile Asn Tyr Asn Gly Asn Thr Asn Leu Asn Pro Ser Leu Lys Ser
1               5                   10                  15

<210> SEQ ID NO 11
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      nucleotide sequence of 8A12 VH CDR2

<400> SEQUENCE: 11
tacataaact acaatggcaa cactaactta aatccatctc tcaaaagt                    48

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid sequence of 8A12 VH CDR3

<400> SEQUENCE: 12

Ser Leu Trp Pro Arg Gly Trp Phe Ala Tyr
1               5                   10

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      nucleotide sequence of 8A12 VH CDR3

<400> SEQUENCE: 13
tcactttggc ccagggggctg gtttgcttac                                      30

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of 8A12 VL

<400> SEQUENCE: 14

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
                20                  25                  30

Leu Ser Trp Phe Gln Gln Lys Pro Gly Lys Ser Pro Lys Thr Leu Met
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys
            100                 105

<210> SEQ ID NO 15
<211> LENGTH: 321
<212> TYPE: DNA
<213> ORGANISM: Artificial Sequence
<220> FEATURE:
<223> OTHER INFORMATION: Description of Artificial Sequence: Synthetic
      nucleotide sequence of 8A12 VL

<400> SEQUENCE: 15
```

```
gacattctga tgacccagtc tccatcttcc atgtatgcat ctctaggaga gagagtcact    60
atcacttgca aggcgagtca ggacattaat agctatttaa gctggttcca gcagaaacca   120
gggaaatctc ctaagaccct gatgtatcgt gcaaacagat tggtagatgg ggtcccatca   180
aggttcagtg gcagtggatc tggccaagat tattctctca ccatcagcag cctggaatat   240
gaagatatgg gaatttatta ttgtctacag tatgatgagt ttcctcggac gttcggtgga   300
ggcaccaagc tggaaatcaa a                                             321
```

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
    amino acid sequence of 8A12 VH

<400> SEQUENCE: 16

```
Asp Val Lys Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Glu
            20                  25                  30

Tyr Ala Trp Thr Trp Ile Arg Gln Phe Pro Gly Asn Lys Leu Glu Trp
        35                  40                  45

Met Gly Tyr Ile Asn Tyr Asn Gly Asn Thr Asn Leu Asn Pro Ser Leu
    50                  55                  60

Lys Ser Arg Ile Ser Ile Ile Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Trp Pro Arg Gly Trp Phe Ala Tyr Trp Gly Gln Gly
            100                 105                 110

Thr Leu Val Thr Val Ser Ala
            115
```

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic
    nucleotide sequence of 8A12 VH

<400> SEQUENCE: 17

```
gatgtgaagc ttcaggagtc gggacctggc ctggtgaaac cttctcagtc tctgtccctc    60
acctgcactg tcactggcta ttcaatcacc agtgagtatg cctggacctg gatccggcag   120
tttccaggaa acaaactgga atggatgggc tacataaact acaatggcaa cactaactta   180
aatccatctc tcaaaagtcg aatctctatc attcgagaca catccaagaa ccagttcttc   240
ctgcagttga attctgtgac aactgaggac acagccacat attactgtgc aagatcactt   300
tggcccaggg gctggtttgc ttactggggc caagggactc tggtcactgt ctctgca      357
```

<210> SEQ ID NO 18
<211> LENGTH: 213
<212> TYPE: PRT
<213> ORGANISM: Artificial Sequence
<220> FEATURE:
<223> OTHER INFORMATION: Description of Artificial Sequence: Synthetic
    Light chain of 8A12 IgG -continued

```
<400> SEQUENCE: 18

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Met
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Arg
                85                  90                  95

Thr Phe Gly Gly Gly Thr Lys Leu Glu Ile Lys Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Arg
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 19
<211> LENGTH: 449
<212> TYPE: PRT
<213> ORGANISM: Artificial Sequence
<220> FEATURE:
<223> OTHER INFORMATION: Description of Artificial Sequence: Synthetic
      Heavy chain of 8A12 IgG

<400> SEQUENCE: 19

Asp Val Lys Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Glu
            20                  25                  30

Tyr Ala Trp Thr Trp Ile Arg Gln Phe Pro Gly Asn Lys Leu Glu Trp
        35                  40                  45

Met Gly Tyr Ile Asn Tyr Asn Gly Asn Thr Asn Leu Asn Pro Ser Leu
    50                  55                  60

Lys Ser Arg Ile Ser Ile Ile Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Leu Trp Pro Arg Gly Trp Phe Ala Tyr Trp Gly Gln Gly
            100                 105                 110

Thr Leu Val Thr Val Ser Ala Ala Lys Thr Thr Ala Pro Ser Val Tyr
        115                 120                 125
```

```
Pro Leu Ala Pro Val Cys Gly Asp Thr Thr Gly Ser Ser Val Thr Leu
        130                 135                 140
Gly Cys Leu Val Lys Gly Tyr Phe Pro Glu Pro Val Thr Leu Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Ser Val Thr Val Thr Ser Ser
            180                 185                 190
Thr Trp Pro Ser Gln Ser Ile Thr Cys Asn Val Ala His Pro Ala Ser
        195                 200                 205
Ser Thr Lys Val Asp Lys Lys Ile Glu Pro Arg Gly Pro Thr Ile Lys
    210                 215                 220
Pro Cys Pro Pro Cys Lys Cys Pro Ala Pro Asn Leu Leu Gly Gly Pro
225                 230                 235                 240
Ser Val Phe Ile Phe Pro Pro Lys Ile Lys Asp Val Leu Met Ile Ser
                245                 250                 255
Leu Ser Pro Ile Val Thr Cys Val Val Val Asp Val Ser Glu Asp Asp
            260                 265                 270
Pro Asp Val Gln Ile Ser Trp Phe Val Asn Asn Val Glu Val His Thr
        275                 280                 285
Ala Gln Thr Gln Thr His Arg Glu Asp Tyr Asn Ser Thr Leu Arg Val
    290                 295                 300
Val Ser Ala Leu Pro Ile Gln His Gln Asp Trp Met Ser Gly Lys Glu
305                 310                 315                 320
Phe Lys Cys Lys Val Asn Asn Lys Asp Leu Pro Ala Pro Ile Glu Arg
                325                 330                 335
Thr Ile Ser Lys Pro Lys Gly Ser Val Arg Ala Pro Gln Val Tyr Val
            340                 345                 350
Leu Pro Pro Pro Glu Glu Glu Met Thr Lys Lys Gln Val Thr Leu Thr
        355                 360                 365
Cys Met Val Thr Asp Phe Met Pro Glu Asp Ile Tyr Val Glu Trp Thr
    370                 375                 380
Asn Asn Gly Lys Thr Glu Leu Asn Tyr Lys Asn Thr Glu Pro Val Leu
385                 390                 395                 400
Asp Ser Asp Gly Ser Tyr Phe Met Tyr Ser Lys Leu Arg Val Glu Lys
                405                 410                 415
Lys Asn Trp Val Glu Arg Asn Ser Tyr Ser Cys Ser Val Val His Glu
            420                 425                 430
Gly Leu His Asn His His Thr Thr Lys Ser Phe Ser Arg Thr Pro Gly
        435                 440                 445
Lys

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      8A12 antibody epitope

<400> SEQUENCE: 20

Lys Gln Gly Asn Ile Val Arg Glu Leu Lys Ala Gln Lys Ala Asp Lys
1               5                   10                  15
Asn Glu Val Ala Ala Glu Val Ala Lys Leu Leu Asp Leu Lys
            20                  25                  30
```

```
<210> SEQ ID NO 21
<211> LENGTH: 174
<212> TYPE: PRT
<213> ORGANISM: Artificial Sequence
<220> FEATURE:
<223> OTHER INFORMATION: Description of Artificial Sequence: Synthetic
      AIMP3(Aminoacyl tRNA synthetase complex-interacting
      multifunctional protein 3)

<400> SEQUENCE: 21

Met Ala Ala Ala Glu Leu Ser Leu Leu Glu Lys Ser Leu Gly Leu
1               5                   10                  15

Ser Lys Gly Asn Lys Tyr Ser Ala Gln Gly Glu Arg Gln Ile Pro Val
                20                  25                  30

Leu Gln Thr Asn Asn Gly Pro Ser Leu Thr Gly Leu Thr Thr Ile Ala
            35                  40                  45

Ala His Leu Val Lys Gln Ala Asn Lys Glu Tyr Leu Leu Gly Ser Thr
        50                  55                  60

Ala Glu Glu Lys Ala Ile Val Gln Gln Trp Leu Glu Tyr Arg Val Thr
65                  70                  75                  80

Gln Val Asp Gly His Ser Ser Lys Asn Asp Ile His Thr Leu Leu Lys
                85                  90                  95

Asp Leu Asn Ser Tyr Leu Glu Asp Lys Val Tyr Leu Thr Gly Tyr Asn
            100                 105                 110

Phe Thr Leu Ala Asp Ile Leu Leu Tyr Tyr Gly Leu His Arg Phe Ile
        115                 120                 125

Val Asp Leu Thr Val Gln Glu Lys Glu Lys Tyr Leu Asn Val Ser Arg
    130                 135                 140

Trp Phe Cys His Ile Gln His Tyr Pro Gly Ile Arg Gln His Leu Ser
145                 150                 155                 160

Ser Val Val Phe Ile Lys Asn Arg Leu Tyr Thr Asn Ser His
                165                 170
```